US012784189B2

(12) United States Patent
Kono et al.

(10) Patent No.: US 12,784,189 B2
(45) Date of Patent: Nov. 3, 2026

(54) IMAGE PROCESSING DEVICE, IMAGE PROCESSING METHOD, PROGRAM, AND IMAGE PROCESSING SYSTEM

(71) Applicant: IMED TECHNOLOGIES, INC., Tokyo (JP)

(72) Inventors: Kenichi Kono, Tokyo (JP); Motohisa Kaneko, Tokyo (JP); Shogo Fukuda, Tokyo (JP); Doowon Jeong, Tokyo (JP); Tomoko Sawayama, Tokyo (JP); Minoru Matsumoto, Tokyo (JP)

(73) Assignee: IMED TECHNOLOGIES, INC., Tokyo (JP)

( * ) Notice: Subject to any disclaimer, the term of this patent is extended or adjusted under 35 U.S.C. 154(b) by 542 days.

(21) Appl. No.: 17/997,765

(22) PCT Filed: May 7, 2021

(86) PCT No.: PCT/JP2021/017451
§ 371 (c)(1),
(2) Date: Nov. 2, 2022

(87) PCT Pub. No.: WO2021/225155
PCT Pub. Date: Nov. 11, 2021

(65) Prior Publication Data

US 2024/0221152 A1 Jul. 4, 2024

(30) Foreign Application Priority Data

May 7, 2020 (JP) ................................ 2020-082171

(51) Int. Cl.
*G06T 7/64* (2017.01)
*G06T 7/00* (2017.01)
(Continued)

(52) U.S. Cl.
CPC .............. *G06T 7/0012* (2013.01); *G06T 7/20* (2013.01); *G06T 7/64* (2017.01); *G06V 10/25* (2022.01);
(Continued)

(58) Field of Classification Search
CPC ........... G06T 7/0012; G06T 7/20; G06T 7/64; G06T 2207/10116; G06T 2207/30021;
(Continued)

(56) References Cited

U.S. PATENT DOCUMENTS

2006/0058633 A1 3/2006 Hoshino et al.
2008/0275467 A1 11/2008 Liao et al.
(Continued)

FOREIGN PATENT DOCUMENTS

CN 103327899 A 9/2013
CN 108471974 A 8/2018
(Continued)

OTHER PUBLICATIONS

Notice of Reasons for Refusal issued in corresponding Japanese patent application No. 2022-052796, dated Sep. 13, 2024.
(Continued)

*Primary Examiner* — Huo Long Chen
(74) *Attorney, Agent, or Firm* — Knobbe, Martens, Olson & Bear, LLP

(57) ABSTRACT

A feature for supporting a healthcare worker during a catheter examination or medical treatment of a blood vessel so as to facilitate concentration on work in an area of attention and provide support in making a determination regarding the area of attention. More specifically, in an image processing apparatus, an image acquisition unit acquires an X-ray image, created on the basis of an absorption rate of X-rays, in which at least a blood vessel and a
(Continued)

device for examining or medically treating the inside of the blood vessel is included in a photographic subject.

18 Claims, 24 Drawing Sheets

(51) Int. Cl.
*G06T 7/20* (2017.01)
*G06V 10/25* (2022.01)
*G06V 10/56* (2022.01)
*G16H 30/40* (2018.01)

(52) U.S. Cl.
CPC ............ *G06V 10/56* (2022.01); *G16H 30/40* (2018.01); *G06T 2207/10116* (2013.01); *G06T 2207/30021* (2013.01); *G06T 2207/30101* (2013.01)

(58) Field of Classification Search
CPC .......... G06T 2207/30101; G06V 10/25; G06V 10/56; G16H 30/40; A61B 2017/00119; A61B 6/545; A61B 34/20; A61B 6/547; A61B 34/25; A61B 2034/2065; A61B 2090/374; A61B 2090/376; A61B 2090/378; A61B 6/463; A61B 6/464; A61B 6/465; A61B 6/469; A61B 6/486; A61B 6/487; A61B 6/504; A61B 90/37; A61B 6/4441; A61B 6/12
See application file for complete search history.

(56) References Cited

U.S. PATENT DOCUMENTS

| | | | | |
|---|---|---|---|---|
| 2009/0005693 | A1 | 1/2009 | Brauner et al. | |
| 2010/0202678 | A1 * | 8/2010 | Kobayashi | G06T 7/70 382/132 |
| 2010/0312095 | A1 * | 12/2010 | Jenkins | A61B 5/418 600/411 |
| 2013/0259336 | A1 * | 10/2013 | Wakai | A61B 6/504 382/130 |
| 2014/0275985 | A1 | 9/2014 | Walker et al. | |
| 2015/0320324 | A1 * | 11/2015 | Jung | A61B 5/02007 600/407 |
| 2016/0192894 | A1 | 7/2016 | Ohishi | |
| 2016/0256120 | A1 | 9/2016 | Stone et al. | |
| 2017/0032523 | A1 | 2/2017 | Klaiman et al. | |
| 2017/0316180 | A1 * | 11/2017 | Takeda | G16H 10/60 |
| 2017/0332945 | A1 | 11/2017 | Gopinathan et al. | |
| 2018/0140260 | A1 | 5/2018 | Taguchi et al. | |
| 2018/0271614 | A1 * | 9/2018 | Kunio | A61B 90/37 |
| 2019/0059839 | A1 * | 2/2019 | Schaefer | A61B 6/503 |
| 2019/0066298 | A1 * | 2/2019 | Snook | H01Q 1/42 |
| 2019/0117181 | A1 * | 4/2019 | Ishii | A61B 6/487 |
| 2019/0201109 | A1 | 7/2019 | Berlinger et al. | |
| 2020/0129740 | A1 | 4/2020 | Kottenstette et al. | |
| 2020/0222018 | A1 * | 7/2020 | van Walsum | A61B 6/5264 |

FOREIGN PATENT DOCUMENTS

| | | | | |
|---|---|---|---|---|
| CN | 111568544 | A * | 8/2020 | A61B 34/10 |
| EP | 3367896 | A1 | 9/2018 | |
| JP | 2002-058658 | A | 2/2002 | |
| JP | 2004-229865 | A | 8/2004 | |
| JP | 2004-283373 | A | 10/2004 | |
| JP | 2007-075141 | A | 3/2007 | |
| JP | 2008-73338 | A | 4/2008 | |
| JP | 2012223616 | A | 11/2012 | |
| JP | 2013-046750 | A | 3/2013 | |
| JP | 2013-056113 | A | 3/2013 | |
| JP | 2013-212364 | A | 10/2013 | |
| JP | 2014-004491 | A | 1/2014 | |
| JP | 2015-503390 | A | 2/2015 | |
| JP | 2015144725 | A | 8/2015 | |
| JP | 2016-123719 | A | 7/2016 | |
| JP | 2017-522943 | A | 8/2017 | |
| JP | 2017185007 | A * | 10/2017 | |
| JP | 2018-29880 | A | 3/2018 | |
| JP | 2018-520809 | A | 8/2018 | |
| JP | 2018-531721 | A | 11/2018 | |
| JP | 2020-062324 | A | 4/2020 | |
| JP | 2020-081448 | A | 6/2020 | |
| JP | 2021-094410 | A | 6/2021 | |
| WO | WO 2017/139894 | A1 | 8/2017 | |
| WO | WO 2020/041615 | A1 | 2/2020 | |
| WO | WO 2021/225155 | A1 | 11/2021 | |

OTHER PUBLICATIONS

International Preliminary Report on Patentability issued in Application No. PCT/JP2021/017451, dated Feb. 28, 2022.

Extended European Search Report in European Patent Application No. 21798936.7 issued on Mar. 26, 2024 in 8 pages.

Sakakaura et al., "Real time artificial intelligence assisted carotid artery stenting: a preliminary experience," J NeuroIntervent Surg 2024;0: pp. 1-5, doi:10.1136/jnis-2024-021600.

Condurache et al., "Fast Detection and Processing of Arbitrary Contrast Agent Injections in Coronary Angiography and Fluoroscopy", in Bildverarbeitung für die Medizin, Springer-Verlag Berlin Heidelberg, 2004 in 2 pages.

Vincent Bismuth, "Image processing algorithms for the visualization of interventional devices in X-ray fluoroscopy", Universite Paris-Est, 2012.

International Preliminary Report on Patentability issued in International Patent Application No. PCT/JP2022/041503, dated May 8, 2023, in 3 pages.

Notice of Reasons for Refusal issued in corresponding Japanese Patent Application No. 2025-025923, dated Sep. 29, 2025.

Office Action issued in Chinese Patent Application No. 202180033882.X, dated May 28, 2026 in 16 pages.

* cited by examiner (a) (b)

IMAGE PROCESSING DEVICE, IMAGE PROCESSING METHOD, PROGRAM, AND IMAGE PROCESSING SYSTEM

This application is the U.S. National Phase under 35 U.S.C. § 371 of International Application PCT/JP2021/017451, filed May 7, 2021, designating the U.S., and published in Japanese as WO 2021/225155 on Nov. 11, 2021 which claims priority to Japanese Patent Application No. 2020-082171, filed May 7, 2020, the entire content of which is incorporated herein by reference.

TECHNICAL FIELD

The present invention relates to an image processing apparatus, an image processing method, a program, and an image processing system, and in particular to an image processing technology for use in the examination or treatment of a blood vessel.

BACKGROUND ART

In recent years, for the examination and treatment of blood vessels in the whole body such as the brain and heart, surgery is being performed where a medical worker such as a physician passes a catheter through the blood vessel of a subject and performs various treatments while displaying the location of the catheter on an X-ray image. In this catheterization surgery, a healthcare professional generally passes a medical device such as a catheter from the inguinal region or upper arm of a subject, and advances the device to a region of interest.

For example, when examining or treating a cerebral blood vessel, a medical worker advances a catheter from the subject's inguinal region or brachial artery through the aortic arch and carotid artery to the cerebral artery. Since a great deal of experience and training is required for healthcare professionals to perform these procedures properly, for example, Patent Document 1 discloses a simulation system for improving the efficiency of surgical procedures performed using a catheter system.

CITATION LIST

Patent Documents

Patent Document 1: International Publication Pamphlet WO 2017/139894

SUMMARY OF THE INVENTION

Problems to be Solved by the Invention

In the examination and treatment of a blood vessel, medical professionals pass a guiding catheter to the target site and then pass multiple devices for examination or treatment such as guide wires, stents, balloons, microcatheters, liquid embolic materials, filters, etc. in the guiding catheter, delivery wires of embolic coils for embolization of aneurysm, etc., and such. That is, in actual examinations and treatments, healthcare professionals need to pay attention to the movements and locations of multiple devices not only when the guiding catheter is passed to the target site but also during the procedure. On the other hand, in order to achieve the original purpose of the examination or treatment, the healthcare professional must concentrate on the work in the area of interest.

Means for Solving the Problems

The present invention has been made in view of these points, and the purpose is to provide a technology for making healthcare professionals concentrate on the work in the area of interest and supporting the judgment of the attention area in the catheter examination or treatment of a blood vessel.

Means for Solving the Problems

The first embodiment of the present invention is an image processing apparatus. This device has an image acquisition unit for acquiring an image that includes at least a device for examination or treatment in a blood vessel as a photographic subject, a region of interest acquisition unit for acquiring one or more regions that include at least a portion of the device in the image as a region of interest, a tracking unit for tracking each of the regions of interest in the image, and a notification unit for notifying a user of the image processing apparatus when at least one of the regions of interest satisfies a condition defined for each of the regions of interest.

When an area including the tip portion of a catheter such as a guiding catheter or the tip portion of a guide wire is set as the region of interest, the notification unit may notify the user on the condition that the region of interest disappears from the image.

When a region including the tip portion of a catheter such as a guiding catheter or the tip portion of a guide wire is set as the region of interest, the notification unit may notify the user on the condition that the distance between the region of interest and the edge of the image is less than a predetermined threshold distance.

The notification unit may notify the user on the condition that at least one of the moving distance, movement speed, and acceleration of the region of interest in the image exceeds the predetermined threshold value.

The notification unit may display the distance between the region of interest and the edge of the image on a display device that displays the image.

The notification unit may change the manner in which the distance is displayed on the display device according to the length of the distance between the region of interest and the edge of the image.

The notification unit may notify the user on the condition that the value obtained by dividing the distance between the region of interest and the edge of the image by the movement speed of the region of interest in the image is less than a predetermined threshold value.

The image processing apparatus may be further equipped with a marker detection unit that detects a marker established on the delivery wire of the embolic coil that approaches a region of interest configured in a portion of the guiding catheter that guides the delivery wire. The tracking unit may further track the detected marker, and the notification unit may notify the user when the embolic coil may be detached from the delivery wire, as triggered by the superimposition of the marker and the region of interest.

The notification unit may notify the user when the marker has passed the region of interest.

The notification unit may display on the display device the distance that the marker should move before detaching the embolic coil from the delivery wire.

When a feature value indicating the shape of the device included in the region of interest satisfies a predetermined condition, the notification unit may notify the user of the image processing apparatus of this fact.

The feature value may be a curvature, and the notification unit may notify the user of the device included in the region of interest on the condition that the curvature of the device exceeds a predetermined threshold curvature or that the curvature is changing but the tip is not moving.

The notification unit may notify the user on the condition that the length of the device in the image or region of interest minus the length of the centerline of the blood vessel in the image or region of interest exceeds a predetermined threshold length.

The notification unit may be equipped with a function of notifying the user by coloring the region of interest with a different color from the image, changing the font, size, or color of the characters displayed, changing the color of the entire screen or part of the screen of the display device, displaying a graphic on the entire screen, outside the frame, or in some other location of the display device, enlarging the region of interest, or changing the color or size of a mark attached to the region of interest.

The notification unit may use sound or vibration for notification.

The second embodiment of the present invention is an image processing method. In this method, a processor of an image processing apparatus performs: a step of acquiring an image that includes at least a device for examination or treatment in a blood vessel as a photographic subject; a step of acquiring one or more regions that include at least a portion of the device in the image as a region of interest; a step of tracking each of the regions of interest in the image; and a step of notifying a user of the image processing apparatus when at least one of the regions of interest satisfies a condition defined for each of the regions of interest.

The third embodiment of the present invention is a program. This program realizes on a computer, a function of acquiring an image that includes at least a device for examination or treatment in a blood vessel as a photographic subject, a function of acquiring one or more regions that include at least a portion of the device in the X-ray image as a region of interest, and a function of tracking each of the regions of interest in the X-ray image, and a function of notifying a user of the computer when at least one of the regions of interest satisfies a condition defined for each of the regions of interest.

In order to provide this program or to update a part of the program, a computer-readable recording medium on which the program is recorded may be provided, or the program may be transmitted over a communication line.

The fourth embodiment of the present invention is an image processing system. This system is equipped with the image processing apparatus described above and an imaging apparatus that captures an image of a person in a state in which a device for examination or treatment in a blood vessel is inserted (an image of the surgical field) and transmits the image to the image processing apparatus.

Any combination of the components disclosed in the present specification, and any conversion of the expression of the present invention between methods, devices, systems, computer programs, data configurations, recording media, or such is also valid as an embodiment of the present invention.

Effects of the Invention

The present invention provides a technology for having medical professionals focus work in the area of interest during catheter examination or treatment of blood vessels, and supporting oversight and delayed judgment in areas other than the area of interest.

MODE FOR CARRYING OUT THE INVENTION

Figure 1:
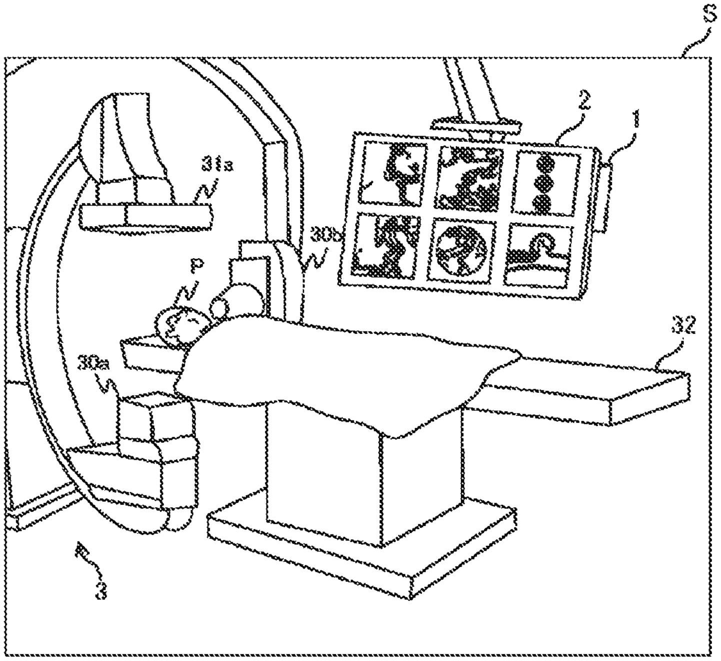
FIG. 1 It is a figure that schematically demonstrates the appearance of an image processing system according to the embodiment.

FIG. 1 is a diagram that schematically shows the appearance of the image processing system S according to the embodiment. The image processing system S includes an image processing apparatus 1, a display device 2, and an X-ray imaging apparatus 3. An outline of the system will be described below with reference to FIG. 1.

The X-ray imaging apparatus 3 is a device for capturing an X-ray image of a test subject P, who is a person in a state in which a device for examination or treatment of blood vessels (hereinafter simply described as "device") is inserted, and transmitting the X-ray image to the image processing apparatus 1. Therefore, the X-ray imaging apparatus 3 is equipped with an X-ray irradiator 30 (a first X-ray irradiator 30*a* and a second X-ray irradiator 30*b*) for irradiating test subject P with X-rays, and an X-ray detector 31 for detecting the X-rays emitted by the X-ray irradiator 30 and a bed 32 for supporting the test subject P.

As shown in FIG. 1, the first X-ray irradiator 30*a* and the second X-ray irradiator 30*b* can irradiate the head of the test subject P with X-rays at different angles of incidence. Here, the X-rays emitted by the first X-ray irradiator 30*a* are detected by the first X-ray detector 31*a* and converted into an X-ray image based on the X-ray absorption rate. The X-rays emitted by the second X-ray irradiator 30*b* are detected by a second X-ray detector not shown and converted into an X-ray image. These X-ray images are displayed on the display device 2. During the medical treatment of the cerebrovascular area, the positions of the first and second X-ray irradiators are generally fixed, and the area of the images displayed on the display device 2 is fixed.

The images generated from X-rays detected by the X-ray detector 31 include the blood vessels (which can be seen by flowing a contrast medium) and tissues such as bones of the test subject P, as well as various types of devices used for blood vessel examination and treatment (for example, catheters such as guiding catheters, guide wires, embolic coils, delivery wires for transporting embolic coils to sites of interest, or such).

The image processing apparatus 1 according to the embodiment is a device for assisting a user who performs catheter examination or treatment of blood vessels (hereinafter, simply referred to as "catheterization surgery", except for the case where there is a distinction between catheter examination of blood vessels and catheter treatment of blood vessels). The image processing apparatus 1 recognizes and/or tracks one or more predetermined regions of interest in the X-ray image generated based on the X-rays detected by the X-ray imaging apparatus 3. By analyzing the X-ray images, the image processing apparatus 1 is triggered when the status of any of the regions of interest satisfies the condition defined for each region of interest, and notifies the user of the image processing apparatus 1, who is a medical professional (hereinafter simply referred to as the "user") of this fact. By setting the region of interest as an area that requires attention other than the area of interest to achieve the purpose of the examination or treatment, the user can concentrate on the work in the area of interest (for example, guiding a microcatheter into an aneurysm, placing a coil into an aneurysm, expanding a balloon, placing a stent, or such).

<Functional Configuration of the Image Processing Apparatus 1 According to the Embodiment>

Figure 2:
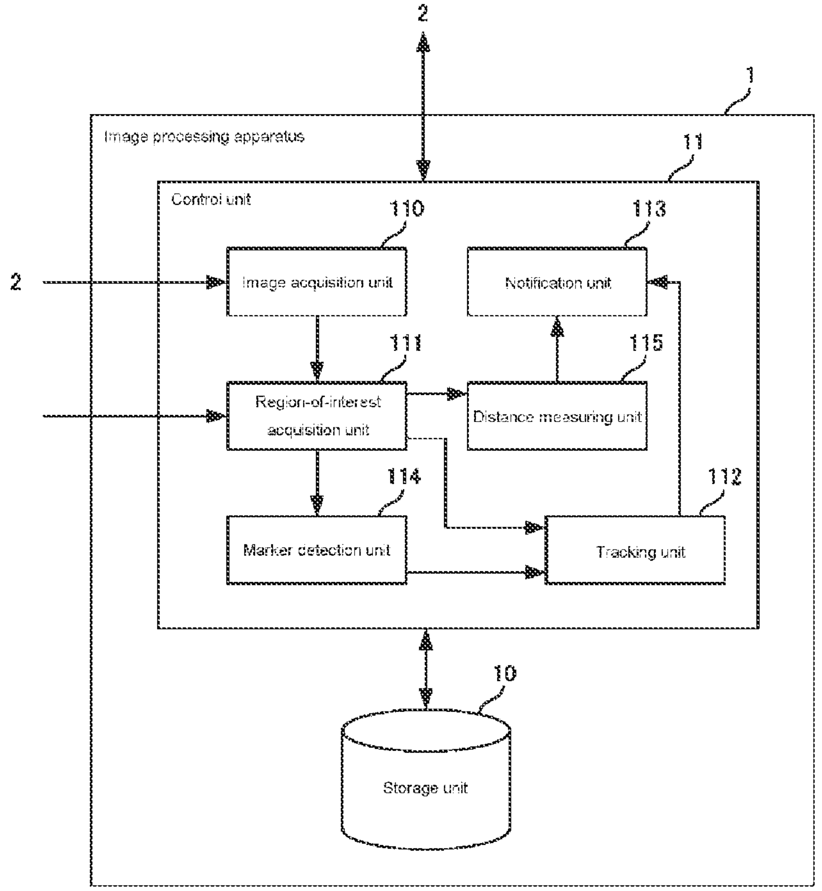
FIG. 2 It is a figure that schematically demonstrates the functional configuration of an image processing system according to the embodiment.

FIG. 2 is a diagram that schematically shows a functional configuration of the image processing apparatus 1 according to the embodiment. The image processing apparatus 1 is equipped with a storage unit 10 and a control unit 11. In FIG. 2, the arrows indicate the main data flows, and there may be data flows that are not shown in FIG. 2. Further, in FIG. 2, each functional block shows a configuration of the functional units, not a configuration of the hardware (device) units. Therefore, the functional blocks shown in FIG. 2 may be mounted in a single device, or may be mounted separately in a plurality of devices. Data can be exchanged between functional blocks via any arbitrary means such as a data bus, a network, and a portable storage medium or such.

The storage unit 10 is a large-capacity storage device such as a ROM (Read Only Memory) that stores the BIOS (Basic Input Output System) of the computer that realizes the image processing apparatus 1, a RAM (Random Access Memory) which is a work area of the image processing apparatus 1, an HDD (Hard Disk Drive) or SSD (Solid State Drive) that stores an OS (Operating System), an application program, and the various information referred to when the application program is executed.

The control unit 11 is a processor or such as a CPU (Central Processing Unit) or GPU (Graphics Processing Unit) of the image processing apparatus 1, and functions as an image acquisition unit 110 by executing the program stored in a storage unit 10, a region of interest acquisition unit 111, a tracking unit 112, a notification unit 113, a marker detection unit 114, and a distance measuring unit 115.

Furthermore, FIG. 2 shows an example in which the image processing apparatus 1 is composed of a single device. However, the image processing apparatus 1 may be materialized by computing resources such as a plurality of processors and memories, for example, a cloud computing system. In this case, each unit constituting the control unit 11 is materialized by executing a program by at least any of the multiple different processors.

The image acquisition unit 110 acquires an X-ray image created based on the absorption rate of X-rays, which includes at least the blood vessel of the test subject P and the device for examination or treatment in the blood vessel as a photographic subject. For example, the X-ray image may include an aneurysm formed in a blood vessel of the test subject P, which is of interest to a healthcare professional, or a narrowed part or infarcted part of the blood vessel. The region of interest acquisition unit 111 acquires one or more regions including at least a portion of the device included in the X-ray image as the region of interest. The region of interest may be established as, for example, the tip of a guide wire (GW), the tip of a guiding catheter (GC), a catheter marker, a coil, etc., but multiple areas, for example, the tip of GC and GW, the tip of two GW and the tip of the GW and the coil may be simultaneously established as the multiple regions of interest. In some embodiments, the region of interest may include blood vessels (vascular lesion areas such as cerebral aneurysms and stenosis) and bones.

Figure 3:
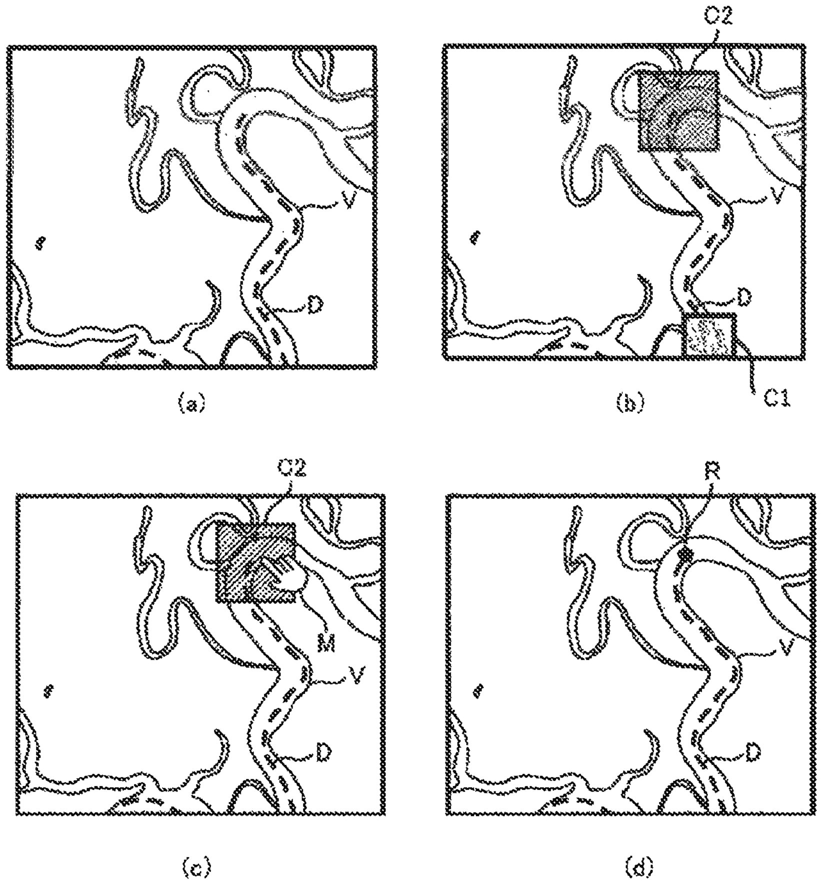
FIG. 3 It is a figure for demonstrating a region of interest.

FIGS. 3 (*a*)-(*d*) are diagrams for explaining the region of interest. Specifically, FIG. 3 (*a*) is a diagram that schematically demonstrates an example of an X-ray image obtained by imaging a blood vessel V. In the example shown in FIG. 3 (*a*), a guide wire, which is one type of device D, is present in the blood vessel V.

Figure 11:
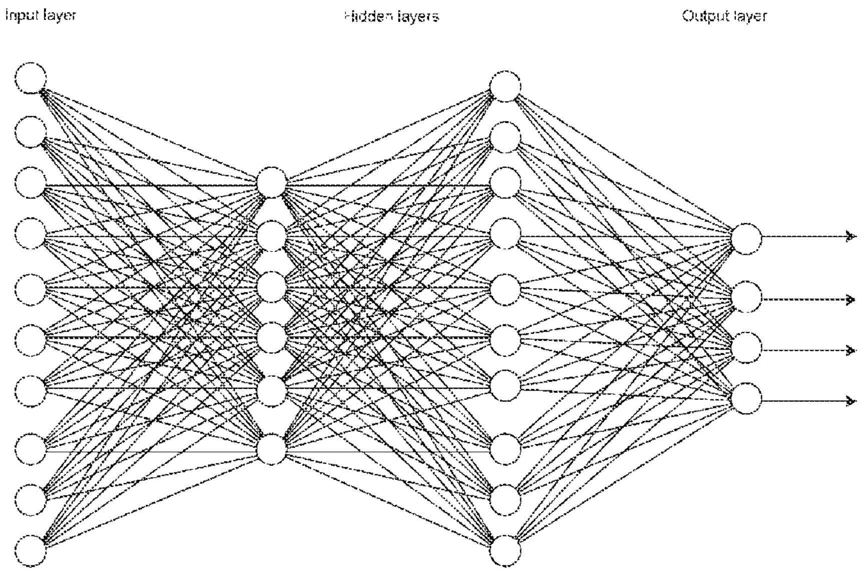
FIG. 11 It is a schematic diagram of a typical neural network.

FIG. 3 (*b*) is a diagram showing an example of a candidate region C which is a candidate region of interest. The region of interest acquisition unit 111 may include a candidate region detector generated by using a known machine learning method such as a neural network (FIG. 11). In FIG. 3 (*b*), the first candidate region C1 (tip of the guiding catheter) and the second candidate region C2 (tip of the guide wire) are shown as candidate regions of interest. This candidate region C is a result obtained by the region of interest acquisition unit 111 of inputting a frame image of an X-ray image to the candidate region detector. Without limitation, as an example, the candidate region detector is learned to detect the tip of a guide wire, the tip of a guiding catheter, a marker of a catheter, and the like.

Detection generally means identifying the position or shape of an object in a single-frame still image in a video. For example, in the detection of the tip of a guide wire, since the guide wire is thin, it may be detected as point coordinates (x, y) on the screen. The detection of the entire guide wire can be done by detecting a bent thin thread-like shape as a one-dimensional curve or as a two-dimensional segmentation.

As the object detection algorithm that can be used in the candidate region detector, for example, algorithms such as Faster R-CNN, YOLO, SSD, U-Net, and ResNet can be used, but without being limited thereto. Further, in implementing the object recognition algorithm, for example, an image processing library such as OpenCV (Open Source Computer Vision Library) may be used.

Faster R-CNN is a CNN (Convolutional Neural Network) that simultaneously cuts out and recognizes regions. A convolutional neural network (CNN) is a neural network with many deep layers composed by piling up layers with some characteristic functions such as “convolutional layers” and “pooling layers”, and it demonstrates excellent performance specifically in the field of image recognition. Faster R-CNN can cut out and recognize a region of interest from the input image in almost real time (about 10 to 20 frames per second). Faster R-CNN enables end-to-end learning from image input to object detection.

YOLO (You Only Look Once) is also a CNN that simultaneously cuts out and recognizes regions. In YOLO, the entire image is divided into grids, and a Bounding Box is sought for each region. YOLO’s CNN architecture enables detection of high-speed objects.

SSD (Single Shot MultiBox Detector) is also a CNN that cuts out and recognizes regions at the same time. SSD can output multi-scale detection frames from the output layers of various levels. SSD puts about 9000 rectangular frames called default boxes with different sizes and shapes on the image, and calculates the predicted value for each of the frames. SSD offers higher speeds by reducing the filter size.

U-Net is a CNN that recognizes an object called segmentation pixel by pixel. It is composed of convolutional layers and has an almost symmetrical Encoder-Decoder configuration. The feature map downsampled through the pooling of the Encoder is upsampled by the Decoder.

FIG. 3 (*c*) is a diagram showing an example of a method for setting the region of interest R. In the example shown in FIG. 3 (*c*), the user selects a second candidate region C2 as the region of interest R. Specifically, the user selects the region of interest R by moving the mouse cursor M to the second candidate region C2 using a pointing device not shown, such as a mouse. The presentation of the candidate region C by the region of interest acquisition unit 111 is arbitrary, and the user may set the region of interest R directly in the X-ray image in a state where the candidate region C is not presented. For example, the region of interest R can be set by drawing a rectangle in the image and designating the region using a pointing device such as a mouse. Alternatively, the region of interest acquisition unit 111 may acquire the output of the candidate region detector generated by using a known machine learning method or the like as the region of interest R.

FIG. 3(*d*) is a diagram showing a region of interest R set by the user. In the example shown in FIG. 3 (*d*), the region of interest R is shown as a black pentagon and is a region that includes the tip portion of the device D. In FIG. 3(*d*), only one region of interest R is set, but the user can set two or more regions of interest R.

The description in FIG. 2 is returned to. The tracking unit 112 tracks each one or more regions of interest R in the X-ray image. The tracking unit 112 can materialize tracking of the region of interest R by using a known image tracking technique. Known image tracking techniques that are available include, but are not limited to, algorithms such as Boosting, MIL, TLD, MedianFlow, KCF, GOTURN, MOSSE, CSRT and the like. The tracking algorithm may be used in combination with the object detection algorithm described above. In implementing the algorithm, for example, a library such as OpenCV (Open Source Computer Vision Library) may be used. Further, it should be noted that, in the context of the present invention, tracking the region of interest R also includes intermittently detecting the region of interest R and identifying its state. Therefore, in some embodiments of the present invention, it is not required that the region of interest R be recognized in all frames of the X-ray image acquired over time. In some embodiments of the invention, tracking of the region of interest R may be performed using a tracking algorithm or an object detection algorithm, or a combination thereof.

The BOOSTING tracker is a tracker based on the online version of AdaBoost (an algorithm used internally by HAAR cascade-based face detector). This classifier is trained at run time using correct and incorrect examples of objects. The first bounding box identified by the user (or another object detection algorithm) is treated as a correct example of the object, and the image outside the bounding box is treated as the background. When a new frame is given, the classifier is applied to all pixels near the previous position and the score is recorded. The new position of the object is the position where the score is maximized. In this way, another correct example of the classifier is obtained. More frames are entered and the classifier is updated by this additional data.

The MIL tracker is based on the same concept as the BOOSTING tracker above. The big difference is that the current position of the object is not just considered as a correct example, but at a small neighborhood around the current position is investigated to generate some potential correct examples. In MIL, instead of specifying correct examples and incorrect examples, a “bag” of correct and incorrect answers is specified. The group of images in the correct bag is not all correct examples. Only one image of the correct bag needs to be an example of the correct answer. The correct bag contains an image centered on the current position of the object and an image of a small neighborhood around it. Even if the current position of the tracked object is not accurate, if a sample near the current position is in the correct bag, there is a high possibility that this bag will contain at least one image of the object properly positioned in the center. The MIL tracker has high performance, does not drift as much as the BOOSTING tracker, and provides reasonable performance even in the event of partial occlusion (shielding).

KFC stands for kernelized correlation filter. This tracker is based on the concepts advocated by the above two trackers. This tracker takes advantage of the fact that a plurality of correct samples used in the MIL tracker has a large overlap area. Such duplicated data provides some excellent mathematical properties, while at the same time making tracking faster and more accurate. It is superior to MIL in both accuracy and speed, and is also excellent in reporting tracking failures.

TLD means tracking/learning/detection. As the name implies, this tracker breaks down the long-term tracking task into three components: (short-term) tracking, learning, and detection. This tracker tracks objects frame by frame. The detector identifies all previously observed appearances and calibrates the tracker as necessary. The detector error is estimated by learning and updated to avoid occurrence of future errors. The output of this tracker tends to be somewhat unstable; for example, if there are other pedestrians in the scene when tracking a pedestrian, this tracker may temporarily track another walker different from the pedestrian to be tracked. The advantage is that it works best even under occlusion (shielding) across multiple frames. The disadvantage is that there are many false positives.

The MEDIANFLOW tracker tracks an object both in the forward direction and backward direction in time and measures the discrepancy between these two trajectories. By minimizing this Forward/Backward error, it is possible to detect tracking failures with certainty and select a reliable trajectory in the video. This tracker performs best when the movement is predictable and small, and when there is no obstruction. Unlike other trackers that continue even when the tracking clearly fails, this tracker can recognize that the tracking has failed.

The GOTURN tracker is an algorithm based on a convolutional neural network (CNN). This tracker is robust to changes of viewpoint, changes of lighting, and deformations, but may not handle shielding (occlusion) well.

The MOSSE (Minimum Output Sum of Squared Error) tracker uses adaptive correlation for object tracking. The MOSSE tracker is robust to lighting, scale, pose changes, and non-rigid deformation. The tracker can also detect occlusions based on the peak-to-sidelobe ratio and resume tracking from where it left off when the object reappears. The MOSSE tracker also works at high frame rates (450 fps or above). The advantage is that it is very easy to implement, as accurately as other complex trackers, and much faster.

The CSRT tracker uses spatial reliability maps for tracking. The CSRT tracker operates at a relatively low frame rate (25 fps), but provides higher accuracy for object tracking.

The notification unit 113 notifies the user of the fact that if at least one of the regions of interest R satisfies the condition determined for each of the regions of interest. Specifically, the notification unit 113 notifies the user, for example, when at least one of the regions of interest R satisfies the condition defined for each of the regions of interest, by displaying a message indicating that fact on the display device 2 or by sounding a notification tone on the speaker of the image processing apparatus 1 not shown. Alternatively, when the user wears a device equipped with a vibrating component such as a smartphone, the user may be notified by vibrating the vibration component. The type, amplitude, and frequency of the notification sound may be changed according to the conditions. The vibration may change the period and amplitude of the vibration according to the conditions.

In this way, by setting the region of interest R in the X-ray image in advance, the user of the image processing apparatus 1 can have the image processing apparatus 1 track the behavior of the set region of interest R, allowing the user to concentrate on working in the area of interest. Further, when displaying the region of interest, the notification unit 113 may color the region of interest with a color different from the color of the acquired image (X-ray image) and display the region of interest. In general, angiographic images are monochrome, and therefore it is very difficult to recognize the device contained in the image. However, by coloring the region of interest, the device can be easily recognized and it will be possible to provide the user with more accurate information. Further, when a plurality of regions of interest is established, the regions of interest may be colored using different colors.

[Specific Example of the Conditions Set in the Region of Interest R]

Next, a specific example of the conditions set in the region of interest R will be described.

In blood vessel catheterization surgery, the user first passes a guiding catheter into the test subject P's blood vessel to the vicinity of the area of interest. Subsequently, the user performs observation (diagnosis) and treatment of the site of interest, for example, coil embolization of a cerebral aneurysm, through another device such as a guide wire, a delivery wire, or a balloon catheter in the guiding catheter.

A catheter is a device that is an elongated tube with a lumen. This catheter is passed through a blood vessel and guided into an aneurysm, for example, a coil is inserted through the lumen of the catheter, and the coil is inserted into the aneurysm to prevent rupture.

There are several types of catheters, but first, the guiding catheter is slightly thick with a diameter of about 2-4 mm, and plays a role of connecting from the puncture site to the front of the target site. A smaller device is inserted into this guiding catheter and guided to the target site. The advantage of guiding catheters is that various devices can be carried via a guiding catheter from the puncture site of a blood vessel in the groin or arm to the vicinity of the target site, and thereby eliminates the need to check the passage one by one. As a result, for example, the treatment can be efficiently performed without moving the fixed screen.

Some guiding catheters have a balloon at the tip (a guiding catheter attached with a balloon), which can stop the flow in the blood vessel and stabilize the guiding catheter.

An intermediate catheter is placed in a guiding catheter and positioned at an area proximally to the target site where the blood vessel is thin, in order to deliver the thinner device to the target site. A plurality of intermediate catheters may be used (gradually become thinner).

A microcatheter is the finest catheter, which is soft and can be inserted into thin blood vessels. A coil or stent is placed in this microcatheter and carried to the target site. An embolic material may also be flushed from the microcatheter.

A balloon catheter has a balloon attached near the tip of a microcatheter, and the balloon is inflated near the target site. As a result, for example, the coil is prevented from coming out of the aneurysm, the stenotic site is dilated, and the blood flow is stopped in the event of vascular perforation to stop bleeding. The balloon usually refers only to the balloon portion of the balloon catheter.

Further, when guiding these catheters, a guide wire of an appropriate size is often used inside. In rare cases, they may be guided by placing them in the flow of blood.

A guide wire is an elongated wire. Typically, guide wires are used to guide a soft catheter to a site of interest, by selecting a vascular bifurcation. In addition, there are delivery wires to carry stents and devices that have a balloon attached to the guide wire to stop blood flow. In the present specification, the term guide wire is defined in a broad sense to include them. The reason for this is that the tips of those guide wires can perforate blood vessels and cause serious complications. Since one of the purposes of the present invention is to support the prevention of such perforation of blood vessels by the tip of such a guide wire, any wire including a thin wire that has a possibility to cause vascular perforation at the tip is referred to as a guide wire.

During the procedure, the blood vessel of the test subject P is present in the body of the test subject P, so that the user cannot directly observe the various devices inserted in the blood vessel. Therefore, as described above, the user can manipulate the device D while viewing the blood vessel V and device D (e.g., guiding catheter, guide wire, coil, catheter, balloon, stent, etc.) that are imaged in the X-ray image generated from X-rays transmitted through the test subject P's body. As shown in FIG. 1, the X-ray imaging apparatus 3 used in catheterization is a device for generating X-ray images of a specific region including the area of interest (e.g., aneurysm, stenosis site, or infarction site in need of treatment) inside the test subject P's body. During the procedure, in many cases, especially in the cerebrovascular region, the area to be acquired as an X-ray image is fixed. Therefore, the entirety of device D is not always captured in the X-ray image that can be observed by the user.

Therefore, when the user is concentrating on a task in the area of interest, such as inserting a coil into an aneurysm or placing a stent, for example, the tip of a guide wire or the tip of a guiding catheter may disappear from the X-ray image because it is out of the angle of view of the X-ray image, and the user may be unable to observe it. In such cases, a vascular perforation at the tip of the device may go unnoticed. Vascular perforation is a serious life-threatening complication. Vascular perforation is most likely to occur at the tip of a device, and it is most likely to occur especially at the tip of a guide wire or catheter. For this reason, the present invention focuses specifically on the tip. There may be multiple tips within a single screen, or the tip of the device may cause vascular perforation at a location other than the operator's area of interest. In addition, in cerebral endovascular treatment, it is necessary to treat while viewing a maximum of four multiple screens at the same time, and it is impossible for the operator to always pay attention to multiple tips in the multiple screens. This support system compensates for that issue with AI and other technologies. Therefore, an example of the conditions established for the region of interest R used in the present invention is a condition related to the distance between the tip of the guiding catheter or the tip of the guide wire and the edge of the X-ray image. Alternatively, the condition may be set to be that the region of interest R exceeds a specific range specified on the X-ray image (for example, a boundary specified by the user with a pointing device such as a mouse) or simply that it moves. That is, in some embodiments of the present invention, not only the edge portion of the image but also the range of any arbitrary region in the image may be treated the same as the edge portion. Further, the boundary line may be a straight line, a curve, a circle, a rectangle, or any other polygon. In some embodiments of the present invention, the distance between the region of interest and the edge of a particular range may be displayed. The manner in which the distance is displayed may vary depending on the length of the distance between the region of interest and the edge of the specific range. In some embodiments of the present invention, the notification unit may notify the user on the condition that the value obtained by dividing the distance between the region of interest and the edge of the specific range by the movement speed of the region of interest in the image is less than a predetermined threshold value. Some embodiments of the present invention include a function to make it easier for the operator to make a decision by making a specific range easier to see by superimposed display or other means. The method of displaying the range may use arrows or such as well as superimposed display, but it is not limited thereto. Further, in some embodiments of the present invention, the distance may be determined by either a straight line distance or a distance along a blood vessel.

Figure 21:
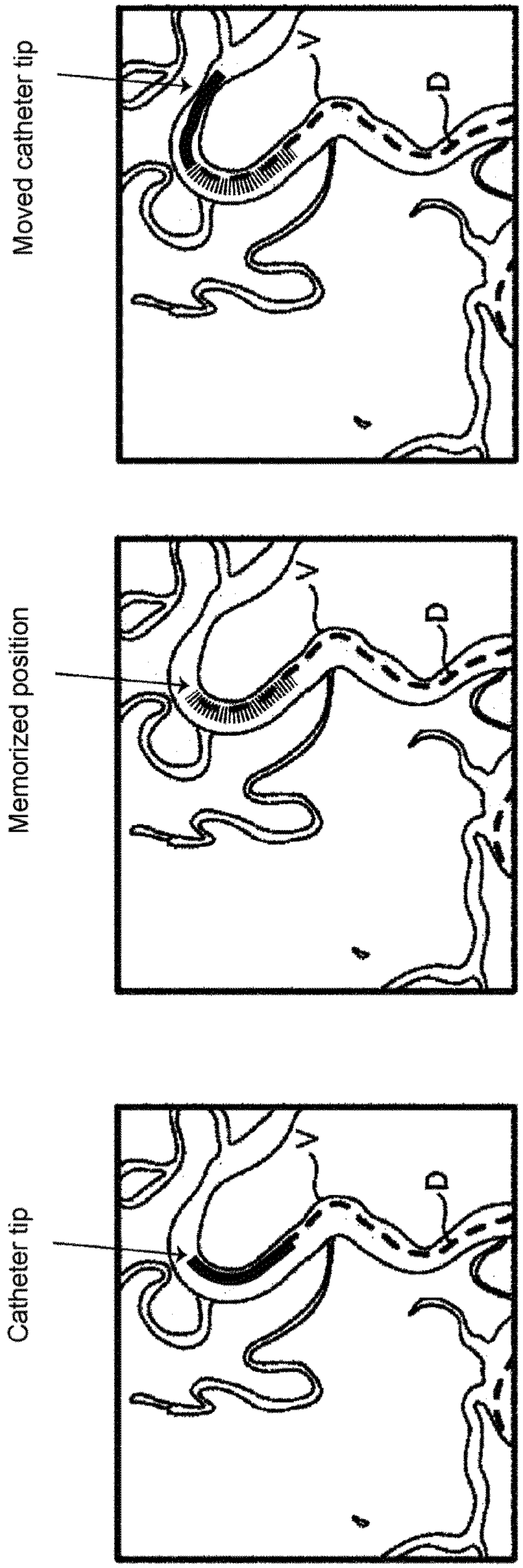
FIG. 21 It is a figure for demonstrating the memory processing of the position and shape of the device according to the embodiment.

Furthermore, by having the location of a device for examination or treatment (also called device of interest) in the vessel, rather than the region of interest, specified automatically or by the user (surgeon/assistant) at a certain point in time, all or part of the device detected at that point in time may be superimposed on the subsequent real-time image. This allows the user (surgeon/assistant) to recognize the movement (deviation) of the device from a specific point in time by superimposing the real-time image and the superimposed display (FIG. 21). The shape of the device may be detected automatically by image analysis or by the surgeon marking it with a mouse or a touch panel. The devices to be superimposed and displayed include, but are not limited to, guide wire tips, markers, stents, guiding catheters, and the like.

For example, suppose that the position and shape of the guide wire tip (black portion) at the time of the left figure in FIG. 21 are memorized. In this case, for example, when the user specifies the guide wire tip with a pointing device such as a touch panel or a mouse, the guide wire tip is recognized and the stored guide wire tip is superimposed on the subsequent X-ray image obtained in real time, as shown in the central figure in FIG. 21. As shown in the right figure in FIG. 21, this makes it easy to visualize and grasp how far the guide wire tip has moved since then.

Thus, in some embodiments of the present invention, the image processing apparatus includes a storage unit that acquires and stores the position and/or shape of a device for examination or treatment in a blood vessel at any point in time, and has the function of superimposing the stored device position and/or shape on images since the acquisition.

For example, in carotid artery stenting, it is important that filters or balloons placed in the distal region of the internal carotid artery remain stable and not move too much to prevent distal embolization (stroke). A notification can be issued if the tip of a guide wire attached to them or their tip moves out of a certain range specified by the surgeon or automatically. In cerebral aneurysm embolization, if the tip of the guide wire in the balloon catheter moves out of the specified range, there is a risk of the balloon slipping, not being returned and perforating the blood vessel at the distal region, and therefore a notification can be issued. Likewise, when inserting a coil, if it moves out of a certain area, a notification can be sent out because it may occlude an important blood vessel. If the coil deviates from the mask image (region) of the aneurysm, a notification can also be issued because of the possibility that the aneurysm may be perforated by the coil, guide wire, or catheter. While it is important that the guiding catheter remains stable for all endovascular procedures, there are times when it is desirable to correct the situation before it disappears outside of the frame, and a notification can be issued if it appears to be moving out of a certain area. In tumor embolization, embolization of cerebral arteriovenous malformation, dural arteriovenous fistula embolization or such, embolization is performed using an embolization material such as liquid or particles, and if the embolization material exceeds the designated area, there is a possibility that it may cause a stroke in an important area, and a notification can be issued. Thus, in some embodiments of the present invention, the device may also include liquid embolic materials, particle embolic materials and such. In addition to the above examples, care is taken in endovascular surgery to keep any arbitrary device, embolic material and such within a designated area and this can be supported.

Figure 4:
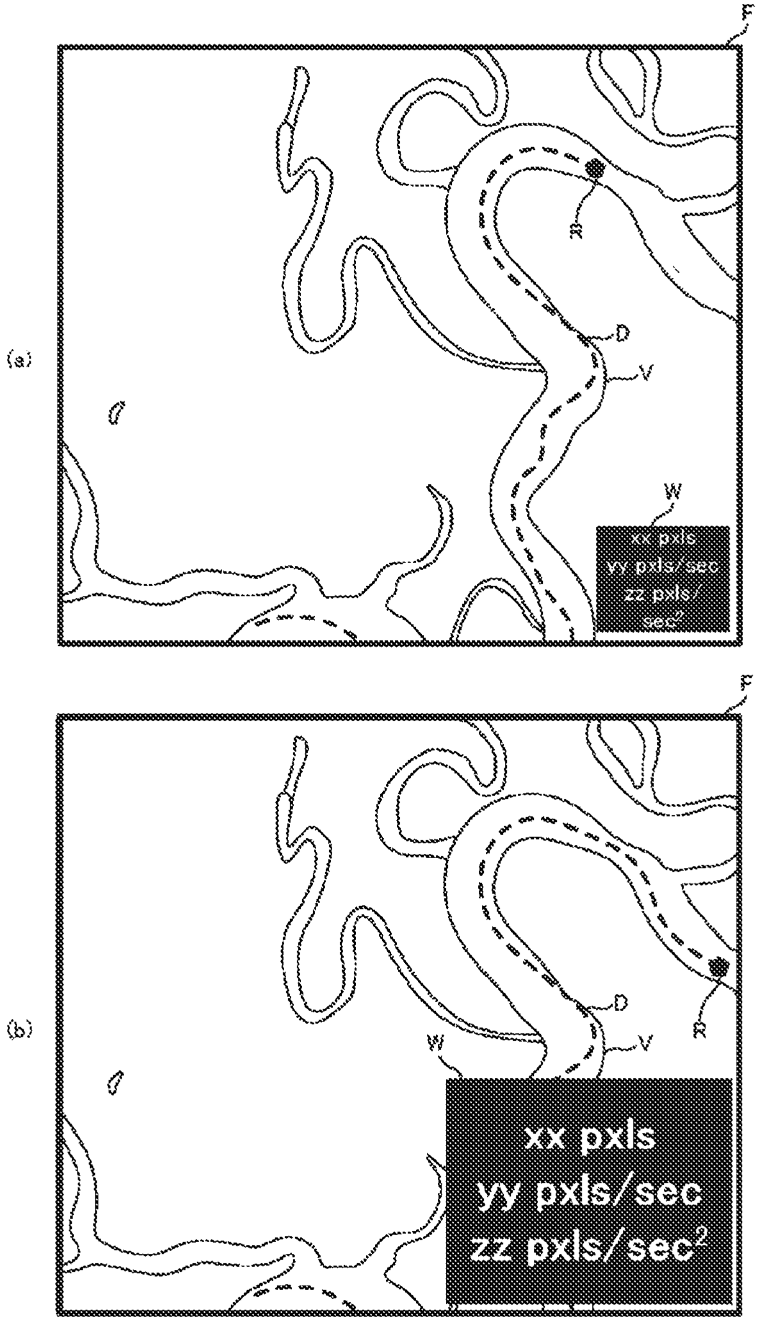
FIG. 4 It is a figure for demonstrating an example of the conditions set in a region of interest.

FIGS. 4(*a*)-(*b*) illustrate an example of the conditions set for the region of interest R. In the example shown in FIG. 4(*a*), the region of interest R is set at the tip portion of the device D. In the example shown in FIG. 4(*a*), information W indicating the speed and acceleration of the region of interest R and the distance (in pixels) between the region of interest R and the edge area F of the X-ray image is superimposed on the X-ray image. Further, FIG. 4(*a*) shows an example when the device D is a guide wire. In some embodiments of the present invention, a specific region specified in the X-ray image may be considered the same as the edge area F of the X-ray image.

The notification unit 113 notifies the user on the condition that the region of interest R disappears from the X-ray image, when a region including the tip portion of the guide wire is set as the region of interest R. In some embodiments, the X-ray image is an image showing a fixed area that includes the region of interest. Usually, during the procedure, the area displayed as the X-ray image is fixed. Further, when a region including the tip portion of the guide wire is set as the region of interest R, the notification unit 113 notifies the user on the condition that the distance between the region of interest R and the edge area F of the X-ray image is less than a predetermined threshold distance.

The "predetermined threshold distance" is a "reference distance for judgment of ejection" established for the notification unit 113 to judge whether or not there is a high probability that the tip of the device will be outside the angle of view of the X-ray image. The specific value of the predetermined threshold distance may be determined by experimentation, taking into consideration the frequency of notification by the notification unit 113 and usability, or such. For example, either the number of pixels in the vertical direction or the number of pixels in the horizontal direction of the X-ray image is 5% of the number of pixels in the other. This allows the user to be notified when the region of interest R, which is an area including the tip portion of a guiding catheter or the tip portion of a guide wire, approaches the edge area F of the X-ray image, before and after the region of interest R is moved out of the edge area F.

The size of movement of the device D in the blood vessel V can be a useful indicator for the user to predict the time it will take for the tip portion of the device D to reach the edge area F of the X-ray image. Specifically, the greater the speed or acceleration of the tip portion of D, the shorter the time until the tip portion of D reaches the edge area F of the X-ray image. Therefore, when a region including the tip portion of a guiding catheter or the tip portion of a guide wire is set as the region of interest R, the notification unit 113 may notify the user on the condition that at least either of the movement speed and the acceleration of the region of interest R in the X-ray image exceeds a predetermined threshold value. As a result, when the movement speed or acceleration of the region of interest R is greater than the threshold value, the user's attention can be drawn before the region of interest R approaches the edge area F of the X-ray image.

Furthermore, the distance between the tip portion of the device D and the edge area F of the X-ray image in the blood vessel V is a useful indicator for the user to determine the probability of the tip portion of device D reaching the edge area F of the X-ray image. Therefore, as shown in the information W in FIG. 4, the notification unit 113 may display the distance between the region of interest R and the edge area F of the X-ray image on the display device 2 which displays the X-ray image.

Here, the "distance between the region of interest R and the edge area F of the X-ray image" may be the distance when the region of interest R moves to the edge area F of the X-ray image along the blood vessel V inserted with the device D in which the region of interest R is set. This can be achieved by the distance measuring unit 115, which extracts the blood vessel V using a blood vessel recognition engine generated in advance using a known machine learning method or the like, and measures the distance from the region of interest R to the edge area F along the blood vessel V. Alternatively, the distance measuring unit 115 may measure the distance described above based on the trajectory of the device D as it travels through the blood vessel V. Specifically, when the user advances a guiding catheter in the blood vessel V, the tracking unit 112 tracks the tip portion of the guiding catheter and stores the trajectory in the storage unit 10. The distance measuring unit 115 may set the length of the trajectory which is included in the region of interest R among the trajectories stored in the storage unit 10 as the length described above.

By having the notification unit 113 display the distance between the tip portion of the device D and the edge area F of the X-ray image on the display device 2, the user can objectively grasp at a glance how far the device D must move to reach the edge area F of the X-ray image. Furthermore, the notification unit 113 may change the display mode of the distance according to the length of the distance between the region of interest R and the edge area F. For example, the font size may be increased as the distance becomes shorter, the color may be changed according to the distance (from blue to yellow to red), the region of interest may be enlarged according to the length of the distance, and the color or size of the mark attached to the region of interest may be changed according to the length of the distance. By working on the above-mentioned mode of display, it can be made easier for the user to notice the change in distance.

In the example shown in FIG. 4(*b*), the region of interest R set at the tip portion of the device D is closer to the edge area F than in the example shown in FIG. 4(*a*). Therefore, the font of the information W, which indicates the speed and acceleration of the region of interest R and the distance (in pixels) between the region of interest R and the edge area F of the X-ray image, is greater than in the example shown in FIG. 4(*a*).

The "distance between the region of interest R and the edge area F of the X-ray image" may be the shortest distance between the region of interest R and the edge area F of the X-ray image, or it may be the length measured along the direction of movement of the region of interest R to the edge area F of the X-ray image. In this case, the blood vessel extraction processing by the distance measuring unit 115 can be omitted, which is advantageous in that it can speed up the processing.

The notification unit 113 may notify the user on the condition that the value obtained by dividing the distance between the region of interest R and the edge area F of the X-ray image by the movement speed of the region of interest R in the X-ray image is less than a predetermined threshold value. The value obtained by dividing the distance between the region of interest R and the edge area F of the X-ray image by the movement speed of the region of interest R in the X-ray image is, so to speak, the expected time until the region of interest R reaches the edge area F of the X-ray image. Therefore, the value of the "predetermined threshold value" is the "grace period for judgment of ejection" established for the notification unit 113 to judge whether or not there is a high probability that the region of interest R will be outside the angle of view of the X-ray image. The specific value of the grace period may be determined by experimentation, taking into consideration the frequency of notification by the notification unit 113 and usability or such, and it is, for example, 3 seconds.

Figure 5:
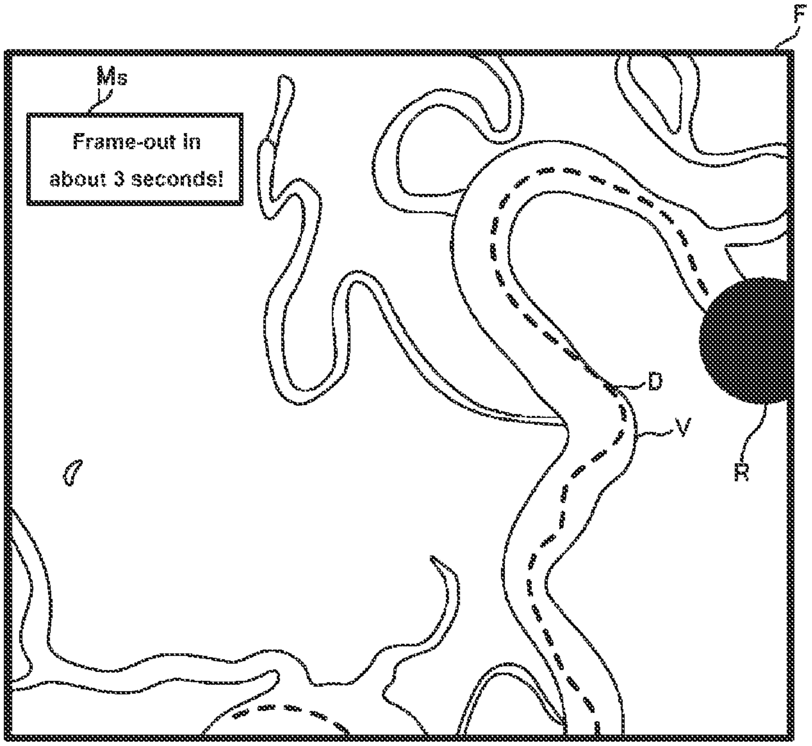
FIG. 5 It is a figure that shows an example of the message which the notification unit notifies.

FIG. 5 shows an example of a message Ms notified by the notification unit 113. In the example shown in FIG. 5, the notification unit 113 displays a message superimposed on the X-ray image indicating that the region of interest R will disappear out of the X-ray image in 3 seconds (so-called frame out). Furthermore, as in the example shown in FIG. 5, the notification unit 113 may change the shape of the region of interest R (changed to a circle in FIG. 5), increase the size of the region of interest R, or change the color of the region of interest R when the region of interest R approaches the edge area F of the X-ray image. This allows the notification unit 113 to make it easier for the surgeon to recognize that the region of interest R is about to frame out.

Figure 6:
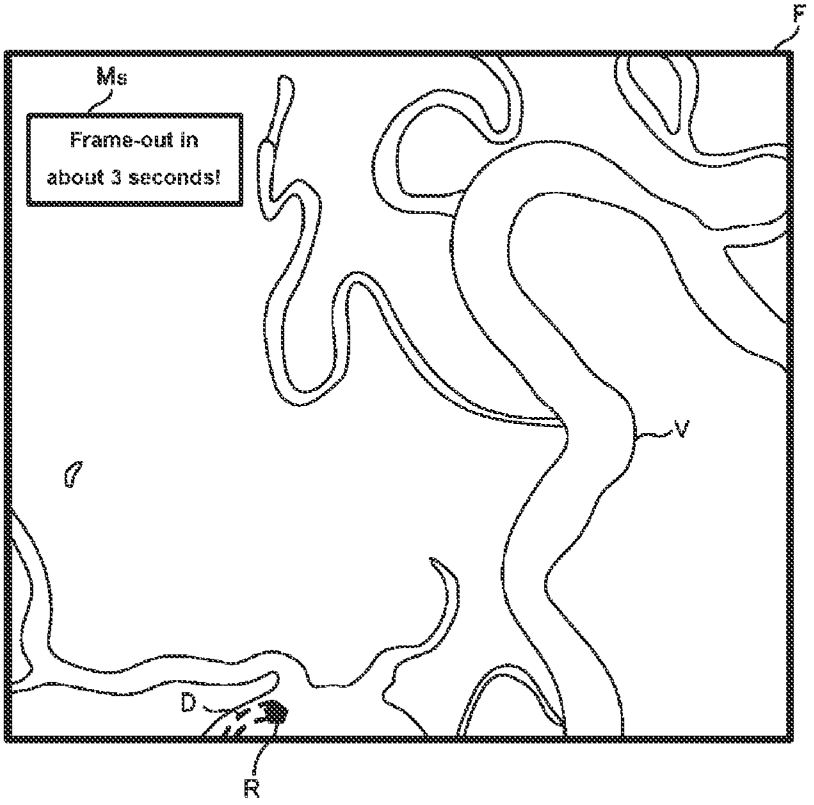
FIG. 6 It is a figure for demonstrating another example of the conditions set in a region of interest.

FIG. 6 is a figure that illustrates another example of the conditions set for the region of interest R. Specifically, FIG. 6 shows an example where the device D is a guiding catheter. Unlike the case of the guide wire shown in FIGS. 4(*a*)-(*b*), the guiding catheter differs in that not only its tip portion but also the entire device D can disappear from the X-ray image. However, whether the device D is a guiding catheter or a guide wire, it is the same in that the tip portion disappears from the X-ray image. Therefore, in the case of a guiding catheter, the region of interest R is set at the tip portion of the catheter as in the case of a guide wire.

Further, in the above example, the threshold is determined based on the distance between the region of interest R and the edge area F of the X-ray image as the "predetermined threshold distance" mainly from the viewpoint of preventing frame-out of the surgical instrument. However, attention is paid to the distance moved in the region of interest R itself, and the threshold value can also be configured to issue a notification to the user when the distance moved in the region of interest R becomes greater than a predetermined threshold. For example, in the state at which the tip of a catheter is inside an aneurysm, when a stent is about to be deployed, it is necessary to take care so that the tip of the catheter does not come out of the aneurysm, but at this time, the surgeon is looking at the stent and cannot follow the movement of the catheter tip with his eyes. In such a case, by configuring issuance of a notification to the user when the movement distance of the region of interest set at the tip of the catheter exceeds a predetermined movement distance, the user can immediately notice the abnormality when the tip of the catheter is about to come out of the aneurysm. The threshold for the movement distance may be set after the region of interest (for example, the tip of the catheter) reaches a predetermined position (for example, within the aneurysm), based on the position reached.

(Guiding of the Embolic Coil)

Next, as another example of the conditions set for the region of interest R, the conditions related to the guiding catheter that guides the delivery wire for the embolic coil are described.

As a catheter treatment for a cerebral aneurysm, embolization in which an embolic coil is filled into the cerebral aneurysm is known. This treatment involves passing a guiding catheter to the vicinity of the cerebral aneurysm, which is the site of interest, passing the delivery wire of the embolic coil through the guiding catheter, and detaching and filling the embolic coil into the cerebral aneurysm. It is an operation aimed to block the inflow of blood into a cerebral aneurysm.

Figure 7:
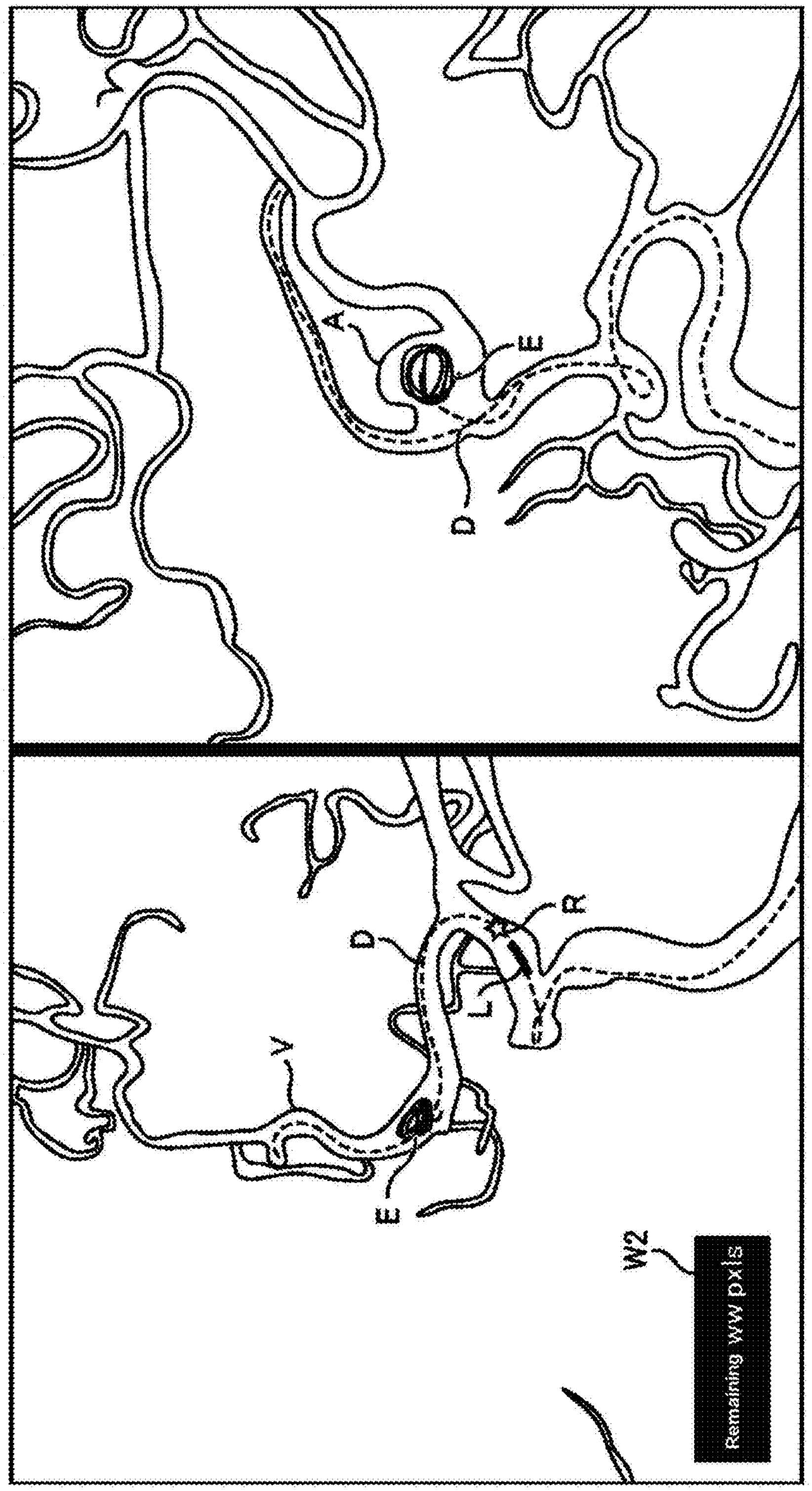
FIG. 7 It is a figure for demonstrating another example of the conditions set in a region of interest.

FIGS. 7(*a*)-(*b*) schematically show an example of an X-ray image in which a guiding catheter that guides the delivery wire of the coil for embolization is imaged, and is a figure for illustrating another example of the conditions set for the region of interest R.

As described above, the X-ray imaging apparatus 3 can irradiate the head of the test subject P with X-rays at different angles of incidence. FIGS. 7(*a*) and 7(*b*) illustrate examples of X-ray images taken by irradiating the head of test subject P with X-rays at different angles of incidence from each other. The user performs the embolization procedure while viewing the two images shown in FIGS. 7(*a*) and 7(*b*).).

In FIG. 7 (*b*), the aneurysm is indicated by the symbol A. The user embolizes the aneurysm A by placing a plurality of embolic coils E inside the aneurysm A. Here, since the aneurysm A can be observed in the X-ray image shown in FIG. 7(*b*), the user focuses on one X-ray image among the two X-ray images.

The delivery wire used to transport the embolic coil E to the aneurysm A is coupled to the embolic coil E at its tip, and the user performs a task of detaching the embolic coil E from the delivery wire after transporting the embolic coil E to the aneurysm A. As shown in FIGS. 7(*a*)-(*b*), when the embolic coil E reaches the aneurysm A, the position of the embolic coil E being transported becomes unclear in the X-ray image due to the other embolic coils E that are already in place in the aneurysm A. For this reason, the delivery wire of the embolic coil E is pre-equipped with a marker L to determine the timing for detaching the embolic coil E. The user uses the marker L on the delivery wire, rather than the embolic coil E itself in the X-ray image, as a landmark to determine the timing for detaching the embolic coil E.

However, as shown in FIGS. 7 (*a*)-(*b*), it is possible that the X-ray image in which the aneurysm A can be observed and the X-ray image in which the marker L can be observed are different. Further, even within the same screen, the positions of the aneurysm A and the marker L are separated, and it may be difficult to observe two points at the same time. Therefore, the user of the image processing apparatus 1 first sets the region of interest R in a portion of the guiding catheter that guides the delivery wire of the embolic coil E. Specifically, the user sets the region of interest R at a position where the marker L and the region of interest R overlap at the timing of detaching the embolic coil E from the delivery wire.

The region of interest acquisition unit 111 receives the region of interest R set in a part of the guiding catheter that guides the delivery wire. The region of interest R can be designated using, for example, a pointing device such as a mouse, a touch panel, or the like. In FIG. 7 (*a*), the region of interest R is indicated by a white star. The marker detection unit 114 detects the marker L that approaches the region of interest R among the markers L provided on the delivery wire of the embolic coil E for embolizing the aneurysm. Further, the tracking unit 112 tracks the marker L detected by the marker detection unit 114.

The notification unit 113 notifies the user of the timing for cutting and detaching the embolic coil E from the delivery wire based on the positional relationship between the marker L and the region of interest R, triggered by the superimposition of the marker L and the region of interest R.

Figure 8:
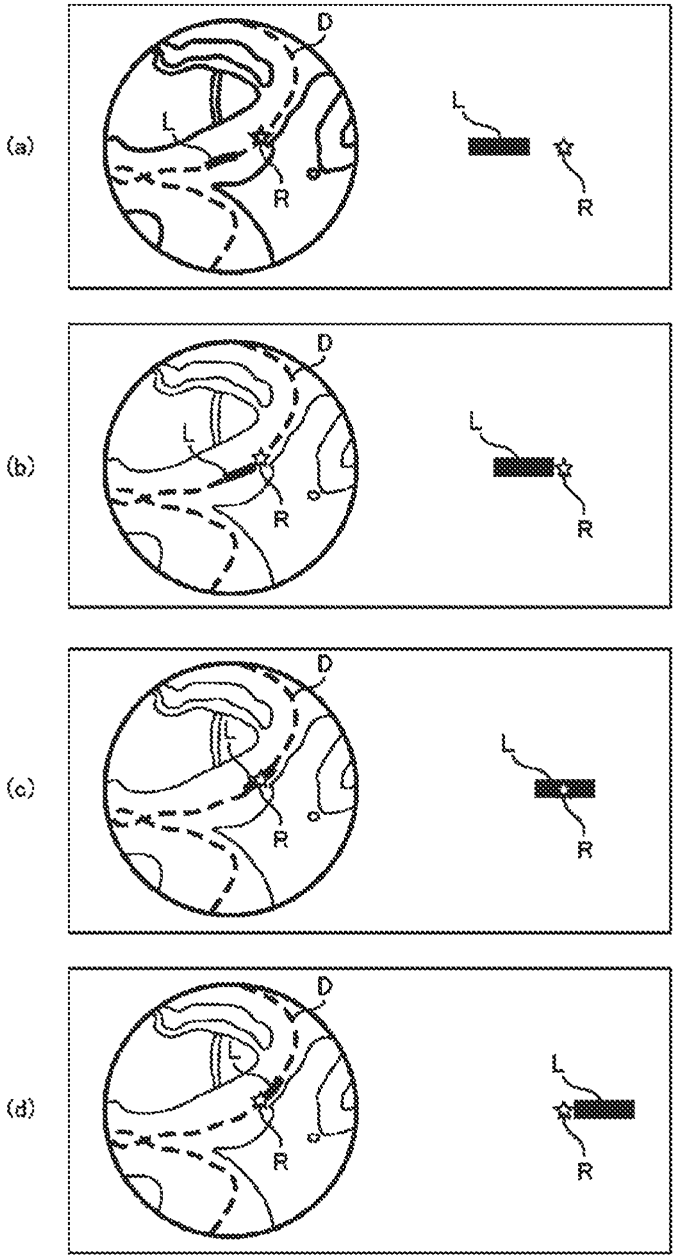
FIG. 8 It is a figure for demonstrating the timing of detachment of an embolic coil.

FIGS. 8(*a*)-(*d*) are figures for illustrating the timing for detaching the embolic coil E. The device D, shown in dashed lines in FIGS. 8(*a*)-(*d*), is a delivery wire. As shown in FIGS. 8(*a*)-(*d*), the delivery wire is marked with a marker L at a certain section on the wire. FIGS. 8(*a*)-(*d*) show a general example of the marker L. In addition, it may be a single dotted line "- . -" or a long straight line.

When the user moves the delivery wire, the marker L also moves in the X-ray image in conjunction with the movement of the delivery wire. On the other hand, the guiding catheter used to guide the delivery wire may move slightly due to friction or other reasons as the delivery wire moves, but the amount of movement is small compared to the movement of the delivery wire. Therefore, the user sets the region of interest R in advance at the position of the guiding catheter corresponding to the position where the marker L should be when the embolic coil E reaches the aneurysm A.

As shown in FIG. 8(*a*)-(*d*), the marker L is present over a certain section on the wire. When the user moves the delivery wire, the tip portion of the marker L comes into contact with the region of interest R, as shown in FIG. 8(*b*). This indicates that the embolic coil E has come close to the aneurysm A.

When the user further moves the delivery wire, the marker L and the region of interest R are superimposed, as shown in FIG. 8(*c*). The notification unit 113 takes the superimposition of the marker L and the region of interest R as a trigger to begin the action of notifying the user of the timing for cutting and detaching the embolic coil E from the delivery wire.

Specifically, as shown by the symbol W2 in FIG. 7(*a*), the notification unit 113 causes the display device 2 to show information W2 indicating the distance that the marker L should travel before the embolic coil E is cut from the delivery wire, as triggered by the superimposition of the marker L and the region of interest R.

More specifically, the user sets the region of interest R so that the end portion of the marker L passes through the region of interest R just when the embolic coil E reaches the aneurysm A, as shown in FIG. 8(*d*). In this case, the information W2 displayed by the notification unit 113 on the display device 2 will show the distance until the end portion of the marker L passes through the region of interest R.

When the marker L passes through the region of interest R, the notification unit 113 further notifies the user of this fact. This allows the user to notice the timing for detaching the embolic coil E from the delivery wire, even if the user is concentrating on the image of the aneurysm A taken as shown in FIG. 7(*b*).

(Shape of the Device D)

Next, as yet another example of the conditions set for the region of interest R, conditions related to the shape of the device D (for example, guide wire) will be described.

When a feature value indicating the shape of the device D included in the region of interest R satisfies a predetermined condition, the notification unit 113 notifies the user of the image processing apparatus 1 of this fact. Specifically, the notification unit 113 notifies based on the curvature of the device D included in the region of interest R or a feature value indicating the "deflection" of the device D included in the region of interest.

When the user tries to advance the device D while the tip portion of the device D is caught in a vessel wall or the like, the tip part of the device D is bent. Generally, when the tip portion of the device D is bent, elastic energy is accumulated in that portion. The more the tip portion of device D bends, i.e., the greater the curvature (smaller the radius of curvature) of the device D, the greater the amount of this elastic energy is accumulated. As the accumulated amount of elastic energy increases, the elastic force of the device D can cause release of connection of the tip portion and the tip part may move at a higher speed. As a result, the tip portion of the device D may suddenly disappear from the X-ray image.

Therefore, the notification unit 113 notifies the user on the condition that the curvature of the device D included in the region of interest exceeds a predetermined threshold curvature or that the curvature is changing but the tip is not moving. It is also possible to take into account that the tip of device D is immobile or that the distance moved is lower than a certain threshold value. The "predetermined threshold curvature" is the "reference curvature for judgment of notification" established for the notification unit 113 to judge whether or not there is a high probability that the tip portion of the device D moves at a high speed. The specific value of the predetermined threshold curvature can be determined by experimentation, taking into consideration the frequency of notification by the notification unit 113, usability, material and size of the device D, elastic modulus, or such.

Figure 9:
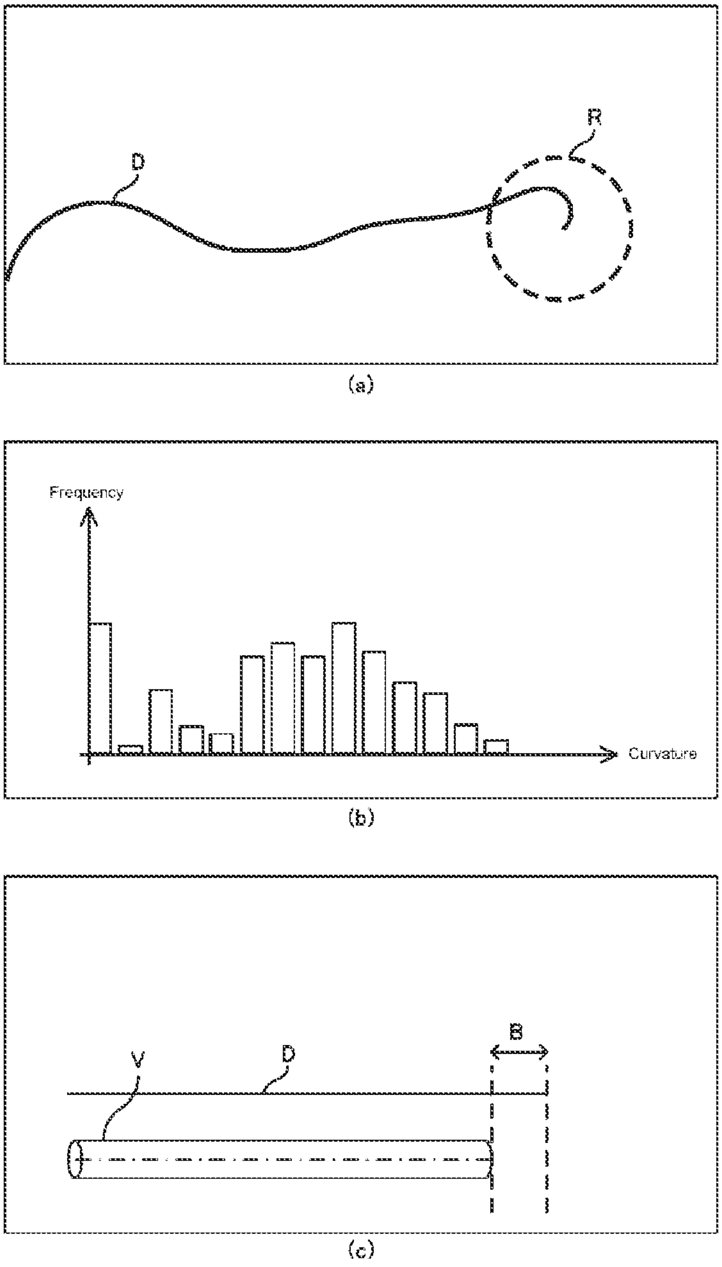
FIG. 9 It is a figure for demonstrating the condition about the shape of the device set in a region of interest.

FIGS. 9(*a*)-(*c*) are figures for illustrating conditions related to the shape of device D set in the region of interest R. Specifically, FIGS. 9(*a*)-(*b*) are figures for illustrating notifications based on the curvature of the device D. In FIG. 9(*a*), the region of interest R is indicated by a dashed circle. Without limitations, as an example, the region of interest R in FIG. 9(*a*) is a circle with a radius of 1 cm centered at the tip portion of the device D. FIG. 9(*b*) is a histogram showing the distribution of the curvature of the device D included in the region of interest R. Specifically, FIG. 9(*b*) shows the distribution of the radius of curvature of the device D in each small region by dividing the device D included in the region of interest R into multiple small regions and determining the radius of curvature of the device D in each small region.

In the histogram showing the distribution of the curvature of the device D, the notification unit 113 notifies the user on the condition that a feature value calculated from the distribution of the curvature (for example, a statistic such as an average value, a mode value, or a median value of the curvature) exceeds a predetermined threshold curvature or that the tip does not move despite a change in the curvature. In this way, the image processing apparatus 1 can provide a trigger for the user to notice the state in which the elastic force is accumulating in the device D.

Further, the notification unit 113 may also notify the user on the condition that the value obtained by subtracting the length of the center line of the blood vessel V included in the region of interest R from the length of the device D included in the region of interest R exceeds a predetermined threshold length (threshold value). FIG. 9(*c*) is a schematic diagram showing the relationship between the length of the device D included in the region of interest R and the length of the center line of the blood vessel V included in the region of interest R. Although the device D and blood vessel are bent in the body of test subject P, for the convenience of explanation, the device D and blood vessel V are shown as straight lines in FIG. 9(*c*). Further, in FIG. 9(*c*), the center line of the blood vessel V is shown as a single dotted line.

The distance measuring unit 115 uses a blood vessel recognition engine to extract the blood vessel V in the region of interest R and track its center line to obtain its length D1. Similarly, the distance measuring unit 115 uses a device recognition engine generated using a known machine learning method or the like to extract the device D and obtain its length D2.

Generally, when a user advances a device D in a blood vessel V, the device D will meander along the wall of the blood vessel V. Therefore, the length D2 of the device D in the blood vessel V is longer than the length of the blood vessel V (length of the center line of the blood vessel V) D1, which means that the device D is deflected in the blood vessel V and elastic energy is accumulated in the device D. As the amount of this deflection increases, it is possible that some trigger will release the elastic energy and cause the device D to move significantly. As a result, the tip portion of the device D may disappear from the X-ray image.

The differential length B, which is the length D1 subtracted from the length D2 calculated by the distance measuring unit 115, can serve as an indicator of the amount of deflection of the device D in the blood vessel V. Therefore, the notification unit 113 displays the length B, which is the length D2 calculated by the distance measuring unit 115 minus the length D1, and if it is longer than the predetermined threshold length, it notifies the user of this fact. In this way, the image processing apparatus 1 can provide an opportunity for the user to notice that elastic force is accumulating in the device D.

(Estimation of the Catheter Tip Position Using a 2nd Marker)

Aneurysm embolization catheters are marked with a tip marker (1st marker) and a 2nd marker (usually at a position 3 cm from the tip). It is important for the surgeon to know where the tip of the catheter is located within the aneurysm in order to perform the procedure safely. However, when the coil enters the aneurysm, the location of the tip marker becomes difficult to find and safety is reduced (see FIG. 17). For example, if the tip marker moves deeper into the aneurysm, the tip, or the coil coming out of the tip, can perforate the aneurysm, leading to a serious complication of subarachnoid hemorrhage. Conversely, if the tip marker is about to exit the aneurysm, the catheter or coil must be dislodged from the aneurysm and reinserted into the aneurysm, and this operation involves the risk of perforation of the aneurysm wall.

Figure 17:
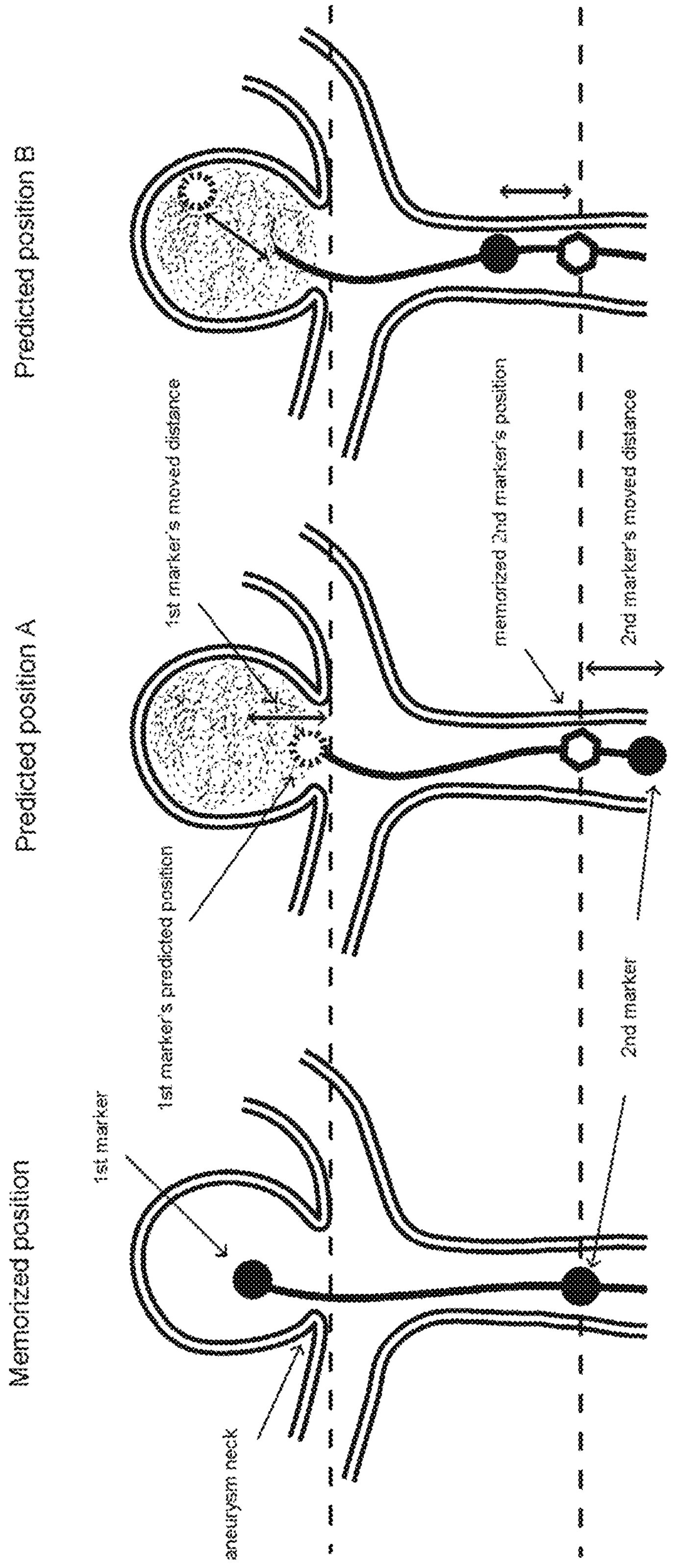
FIG. 17 It is a figure for demonstrating an example of estimation of the catheter tip position using the 2nd marker according to the embodiment.

For example, in FIG. 17, the figure on the left shows the state in which the microcatheter is inserted into an aneurysm. The size of the aneurysm could be, for example, 10 mm. The distance between the 1st marker and 2nd marker attached to the microcatheter is constant (usually 30 mm). For example, suppose that the positions of the 1st marker and 2nd marker are recorded in this state, respectively (memorized position). The middle figure in FIG. 17 shows the state in which the position of the microcatheter has moved. Once the coil enters the aneurysm, the position of the 1st marker becomes invisible or hard to see. Therefore, the position of the 1st marker is estimated from the difference between the position of the 2nd marker at this point and the previously stored position of the 2nd marker. In this case, the 1st marker is predicted to be at a place approximately 0 mm from the aneurysm neck (predicted position A). The figure on the right also shows the state in which the position of the microcatheter moved. Similarly, the position of the 1st marker is estimated based on the distance moved by the 2nd marker. In this case, it is estimated to be 8 mm from the aneurysm neck.

Some embodiments of the present invention relate to a method for estimating the tip position from the movement of the 2nd marker when the tip of the catheter is in the coil (aneurysm) and its position is unknown. More specifically, it relates to a method for estimating the tip position of a catheter, comprising a step of storing the positional relationship between the tip of the catheter and the 2nd marker (for example, 3 cm apart), a step of storing the distance a between the neckline of the aneurysm and the 1st marker and the position of the 2nd marker at that time t1, a step of calculating the distance b of movement from the position of the 2nd marker at time t2, and a step of estimating the distance a-b from the aneurysm neckline to the tip of the catheter, and a step of notifying the user of the estimated distance. Here, the catheter tip, 2nd marker, and aneurysm neckline can be automatically detected by image recognition by a computer. Alternatively, they can be specified manually by a pointing device such as a mouse or a touch panel. The estimated distance a-b can be displayed on a display device. In addition, the position of the catheter tip, estimated based on the estimated distance a-b, may be displayed on the display device. An arbitrary threshold value may be set and notified when the distance deviates from it, and the speed and acceleration may be determined in addition to the distance and notified according to the value (rapid or large movements are likely to be dangerous). The distance moved can be a straight line or a distance along the curve of the catheter. Since the curved shape of the catheter may change, the length of the curve may also be used. Furthermore, the distances a, b, and a-b can be probability distributions due to changes in the shape of the catheter. For example, if there are multiple timings to be memorized first, a distribution of the distance a can be made, so the mean and variance can be used to guess the location and predict it as the most likely single point, or it can be displayed as a probability distribution in a heat map or the like. Thus, the estimated distance may be expressed by a probability distribution, and the estimated position of the catheter tip may be colored like a heat map and displayed based on the probability distribution.

In addition to measuring the distance moved, the position of the 2nd marker may be specified by the surgeon or recognized by the computer, and the position may be indicated on the display device in a semi-transparent superimposition display or by an arrow. The surgeon/assistant visually recognizes whether the tip marker has moved forward or backward by recognizing how much the current 2nd marker has shifted from this fixed display.

Some embodiments of the present invention relate to programs for executing the above methods on a computer. Further, some embodiments of the present invention also relate to an image processing apparatus and a method of operating the same for performing the above methods. Such an image processing apparatus may include, for example, a positional storage unit that stores the positional relationship between the tip of the catheter and the 2nd marker (for example, 3 cm apart), a positional storage unit that stores the distance a between the neckline of the aneurysm and the 1st marker and the position of the 2nd marker at that time t1, a distance estimation unit that calculates the distance moved b from the position of the 2nd marker at time t2 and estimates the distance a-b from the aneurysm neckline to the tip of the catheter, and a notification unit that notifies the user of the estimated distance. Furthermore, some embodiments of the present invention also relate to a cerebral aneurysm coil embolization assistance system that is equipped with the image processing apparatus described above and an image capture device that captures X-ray images of a patient (or test subject P) in the state in which a guiding catheter and a delivery wire for an embolization coil are inserted into a vessel, and transmits the images to the above image processing apparatus.

<Processing Flow of Estimating the Catheter Tip Position Using the 2nd Marker>

Figure 22:
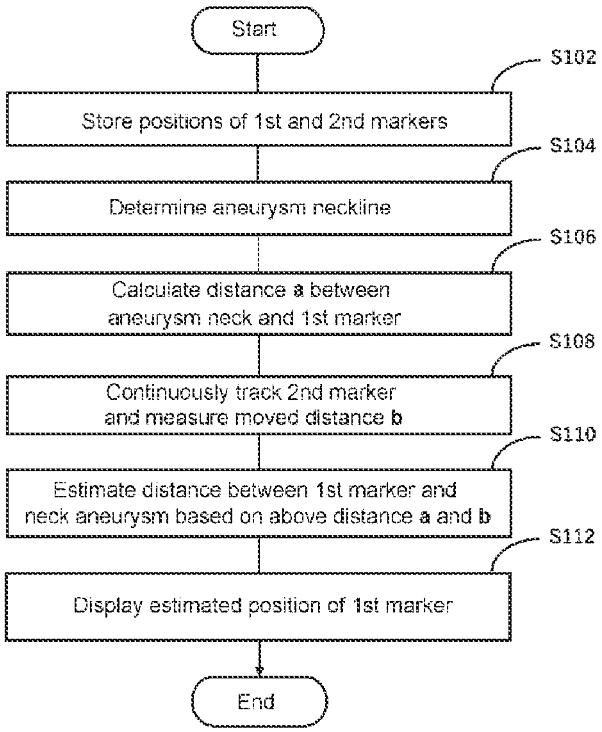
FIG. 22 It is a flowchart for demonstrating the flow of the estimation processing of the catheter tip position using the 2nd marker executed by the image processing apparatus according to the embodiment.

FIG. 22 is a flowchart for explaining the flow of estimation processing of the catheter tip position using the 2nd marker, which is performed by the image processing apparatus according to the embodiment. The processing in this flowchart is started, for example, when the image processing apparatus 1 is started, or when the user or the image processing apparatus 1 determines that the processing needs to be started.

First, the image acquisition unit 110, region of interest acquisition unit 111, and tracking unit 112 function to detect and track the device D for examination or treatment in the blood vessel V by video analysis. Then, the positions of the 1st marker and 2nd marker at that time (T=t1) are stored (S102), either automatically by image analysis or by designation of the user (operator) (S102).

Further, the line of the aneurysm neck is then determined automatically or by designation of the user (surgeon) (S104). Then, the distance A between the line of the aneurysm neck and the 1st marker is calculated (S106). At this time, the straight line or curved line distance A between the line of the aneurysm neck and the 1st marker (usually located within the aneurysm) can be measured.

Next, the 2nd marker is continuously tracked and the distance moved b is measured (S108). The 2nd marker is continuously tracked by image analysis and the movement distance b (straight line or curved line distance) of the 2nd marker at T=t2 is measured. This movement distance may be directional (plus/minus).

Then, based on the above distances A and b, the distance of the 1st marker from the aneurysm neck is estimated (S110). For example, the distance of the 1st marker from the aneurysm neck is estimated to be A-b. Alternatively, it may be inferred that the 1st marker is located at a position that has been moved by b from the position of the 1st marker at T=t1 in a direction perpendicular to the aneurysm neck.

The estimated position of the 1st marker is then displayed (S112). For example, the estimated position of the 1st marker at T=t2 or the distance from the aneurysm neck can be displayed by superimposition or displayed in numerical values. If the 1st marker is about to deviate from the aneurysm near the aneurysm neck or is about to hit the aneurysm wall at the back of the aneurysm, the user (surgeon/assistant) may be additionally notified of this. If the analysis is difficult or if the user (surgeon) specifies otherwise, this function can be temporarily stopped. After this processing is completed, the processing in this flowchart may be started again, if necessary.

(Replay Function)

Since medical personnel pay attention to a specific location during a procedure, if they are not paying attention to the device that issues the warning or are looking at a different screen when the system in this disclosure issues a notification, they will try to understand the situation after the warning occurs. However, because real-time video is updated moment by moment, it is often difficult to see the details around the time when the warning is issued. In addition, depending on the nature of the warning, it may be necessary to ascertain the details of the device operation itself, the difference between the time when the warning occurred and the current time, the time that has elapsed since the warning occurred, and the like.

For example, for the guide wire tip, it is desirable to obtain information on the details of the movement of the tip portion. For example, rapid and large movements increase the risk of vascular perforation. In the case of the disappearance of a guiding catheter, it is desirable to obtain information on the position and elapsed time at the time of the catheter's exit from the image. In the case of a coil detector, it is desirable to obtain information on the deviation from the optimal point.

Figure 12:
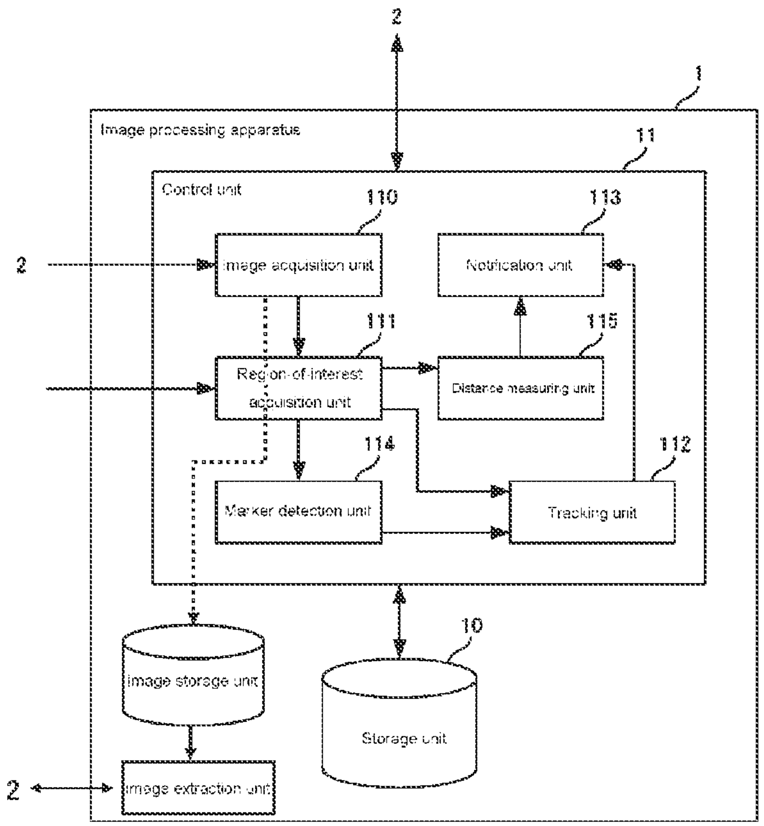
FIG. 12 It is a figure that schematically demonstrates the functional configuration of the image processing apparatus provided with the replay function according to the embodiment.
Figure 13:
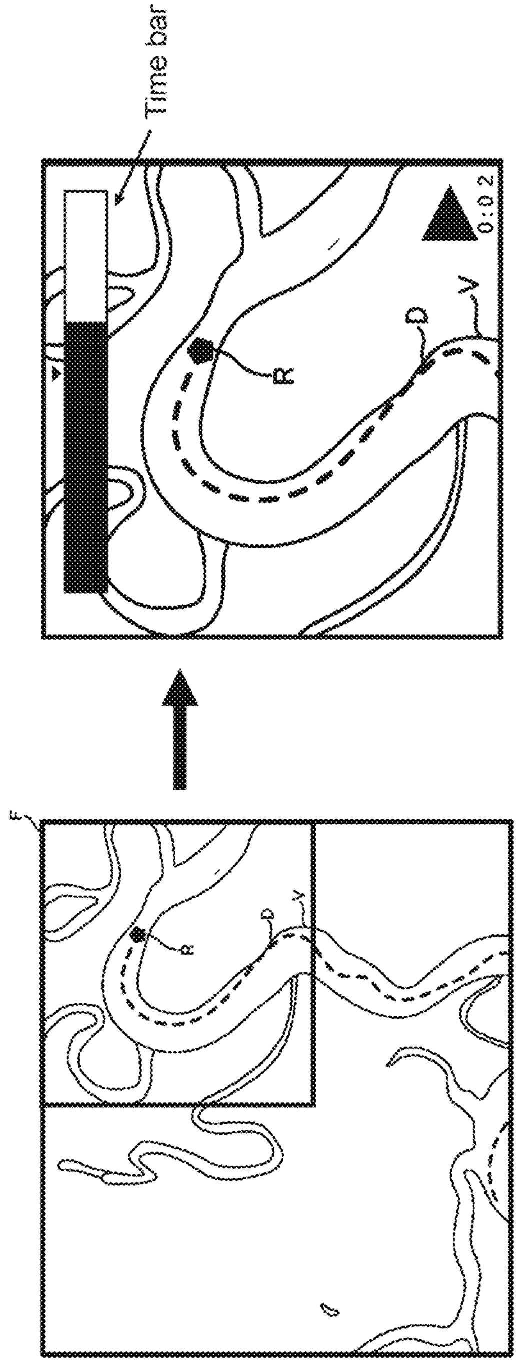
FIG. 13 It is a figure for demonstrating an example of a replay display when a notification occurs.
Figure 14:
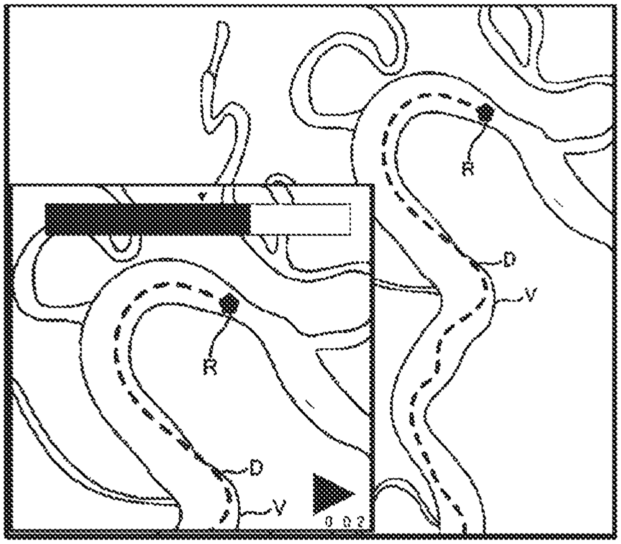
FIG. 14 It is a figure for demonstrating an example of displaying a replay playback window on a real-time display screen.

In some embodiments of the present invention, the image processing apparatus is equipped with a function (i.e., replay function) that allows the surgeon to save the image and recognition information and review it when necessary by providing the information as needed. FIG. 12 shows the configuration of an image processing apparatus further equipped with an image recording unit (which can be integrated with 10) that stores the images obtained from the image acquisition unit 110 and an image extraction unit that extracts some of the images before and after the time the notification occurred. FIG. 13 shows an example of an enlarged display of the replay image at the time the notification occurred, with the region of interest being cropped out at the center. FIG. 14 shows an example of a (an enlarged) replay playback window on the real-time display screen. In this example, the replay is enlarged and displayed in an area as far out of the region of interest as possible, which allows one to determine what happened in the area where the warning was issued within the limited area of one screen.

In some embodiments of the present invention, the image processing apparatus further comprises an image recording unit that stores images (including videos) obtained from the image acquisition unit over time (continuously). In some embodiments of the present invention, the image processing apparatus further comprises an image extraction unit that extracts video images from the image storage unit for a certain period of time before and after the notification was issued by the notification unit. The extraction period and playback speed of the images may be automatically determined based on at least one of the movement distance, movement speed, and acceleration of the region of interest when the notification occurred. The information obtained by the region of interest acquisition unit, the tracking unit, the notification unit, the marker detection unit, and/or the distance measuring unit can also be used in the extraction processing.

In some embodiments of the present invention, the image processing apparatus can display the extracted image on a display device. The extracted image may be automatically displayed a predetermined number of times repeatedly. The extracted image may be displayed based on any arbitrary operation including playback, stop, fast forward, rewind, frame advance, slow playback, and double-speed playback. This allows the user to easily check the images. In addition, the time elapsed from the time when the notification occurred, a comparison of the position of the region of interest at the time when the notification occurred and after any arbitrary elapsed time (the comparison display may include, for example, the relevant area, differences in the detected position, and the alignment of the images themselves), or the trajectory of the region of interest obtained by the tracking unit may be superimposed on the extracted image and further displayed on the display device.

In some embodiments of the present invention, the image processing apparatus can cut out a portion of an area in the vicinity of the region of interest from the extracted image and display it. The extracted image can be displayed in a position that does not interfere with the display of the region of interest. The extracted image may be enlarged and displayed.

In some embodiments of the present invention, the image processing apparatus can display the extracted image simultaneously with the occurrence of the notification or after a predetermined time has elapsed from the occurrence of the notification. In some embodiments of the present invention, the image processing apparatus can simultaneously display the video images taken from multiple directions.

The replay display described above may be used at a time other than at the time of occurrence of the notification. In other words, the image extraction unit may extract images from the image storage unit not only for a certain period of time before and after the notification is issued by the notification unit, but also for any time or period of time. For example, when the user (surgeon) feels the need to do so, he can specify any arbitrary region of interest to view a replay display of the previous scene. This allows the user to grasp and compare what happened in the region of interest while viewing the display in real time.

Some embodiments of the present invention relate to a program for executing the above method on a computer. Further, some embodiments of the present invention also relate to an image processing apparatus and a method of operating the same for executing the above methods.

<Processing Flow of the Replay Display Function>

Figure 23:
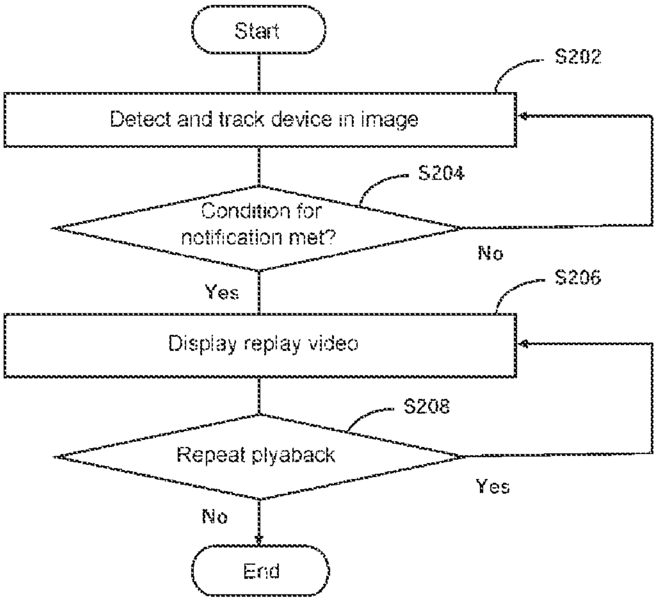
FIG. 23 It is a flowchart for demonstrating the flow of the replay function processing executed by the image processing apparatus according to the embodiment.

FIG. 23 is a flowchart for explaining the flow of processing of the replay function performed by the image processing apparatus according to the embodiment. Processing in this flowchart starts, for example, when the image processing apparatus 1 is started.

First, the image acquisition unit 110, region of interest acquisition unit 111, and tracking unit 112 function to detect and track the device D for examination or treatment in the blood vessel V by video analysis (S202).

Next, it is determined as to whether a notification condition (the distance moved exceeds a threshold value, or such) is met (S204); and if the condition is met, along with the issuance of a notification, a portion of the display screen shows the replay videos before and after the notification condition is met (S206). At this time, the real-time image is displayed as usual, and the replay video may be repeated and displayed several times so that it does not overlap with the area meeting the notification condition, or until the user (surgeon/assistant) wishes (S208). When the repetition is completed, the replay video screen is closed. After completion, the processing in this flowchart may be started again.

(Estimation of the Location of the Region of Interest Outside the Frame)

It is dangerous for the region of interest, such as the tip of a guide wire or the tip of a guiding catheter, to move outside the range of the X-ray angle of view (frame out), but the level of risk depends on the amount of movement. Specifically, for example, if the tip of the guide wire is slightly (within 5 mm or such) outside the frame, the possibility of vascular perforation is low, but if the tip is significantly outside the frame (20 mm or more, or such), the risk of vascular perforation is high, and when the region of interest is framed out, it is necessary to pull it back within the angle of view of the X-ray image, but it may not be possible to deal with it immediately depending on the situation. In such cases, it is important to know how far the framed out region of interest has moved out of the X-ray image angle and how dangerous such movement is. Accordingly, some embodiments of the present invention relate to a device for estimating and displaying the position, speed, and acceleration status of a framed-out region of interest.

Figure 15:
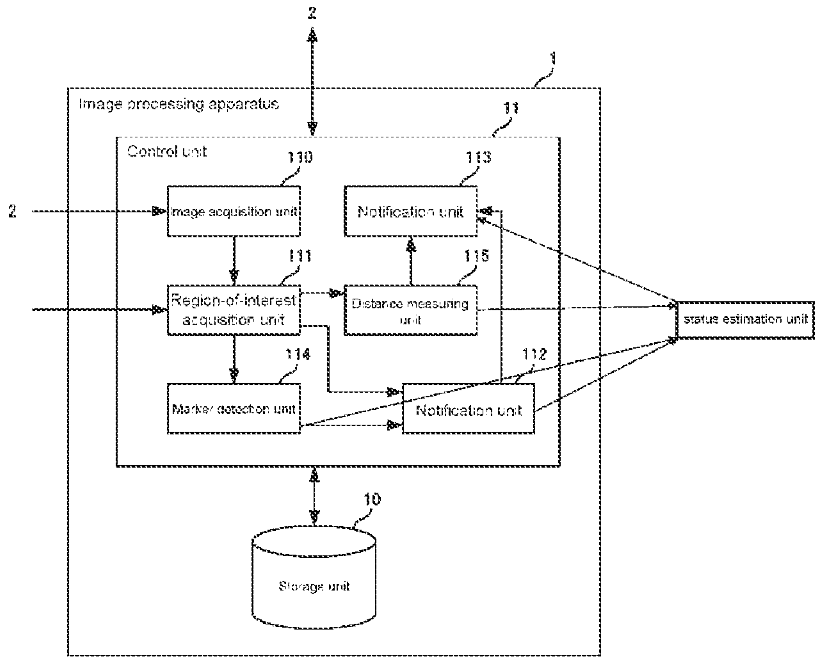
FIG. 15 It is a figure that schematically demonstrates the functional configuration of the image processing apparatus equipped with a status estimation unit according to the embodiment.

The estimation of the position of such an out-of-frame region of interest is performed, for example, by an image processing apparatus, which is an image processing apparatus comprising an image acquisition unit for acquiring an image including at least a device for examination or treatment in a blood vessel as a photographic subject, a region of interest acquisition unit for acquiring one or more regions in the image that include at least a portion of the device as a region of interest, a tracking unit that tracks each of the regions of interest in the image, and a notification unit that notifies the user of the image processing apparatus when a region including the tip portion of a catheter or the tip portion of a guide wire is set as the region of interest, on the condition that the region of interest disappears from the image, and a status estimation unit that estimates the current position and/or speed of the tip portion of the catheter or the tip portion of the guide wire based on the position, speed and/or acceleration of the tip portion of the catheter or the tip portion of the guide wire immediately before the region of interest disappears from the image (FIG. 15). The current position and/or acceleration of the region of interest estimated by the status estimation unit can be displayed on a display device.

Here, the status estimation unit can store the output from the region-of-interest acquisition unit, marker detection unit, and tracking unit chronologically from before the frame-out to estimate the position of the framed-out region-of-interest, and use the stored output to calculate the position, speed, acceleration, and other states of the region-of-interest. When the region of interest frames out and tracking on the screen becomes impossible, the position, speed or such of the region of interest is estimated from the state prior to the frame-out and the user is notified. Estimation methods for this include, but are not limited to, learning-based methods using deep learning (CNN, RNN, WaveNet, or such) and Bayesian estimation methods (Kalman filter, extended Kalman filter, ensemble Kalman filter, particle filter, or such).

Figure 16:
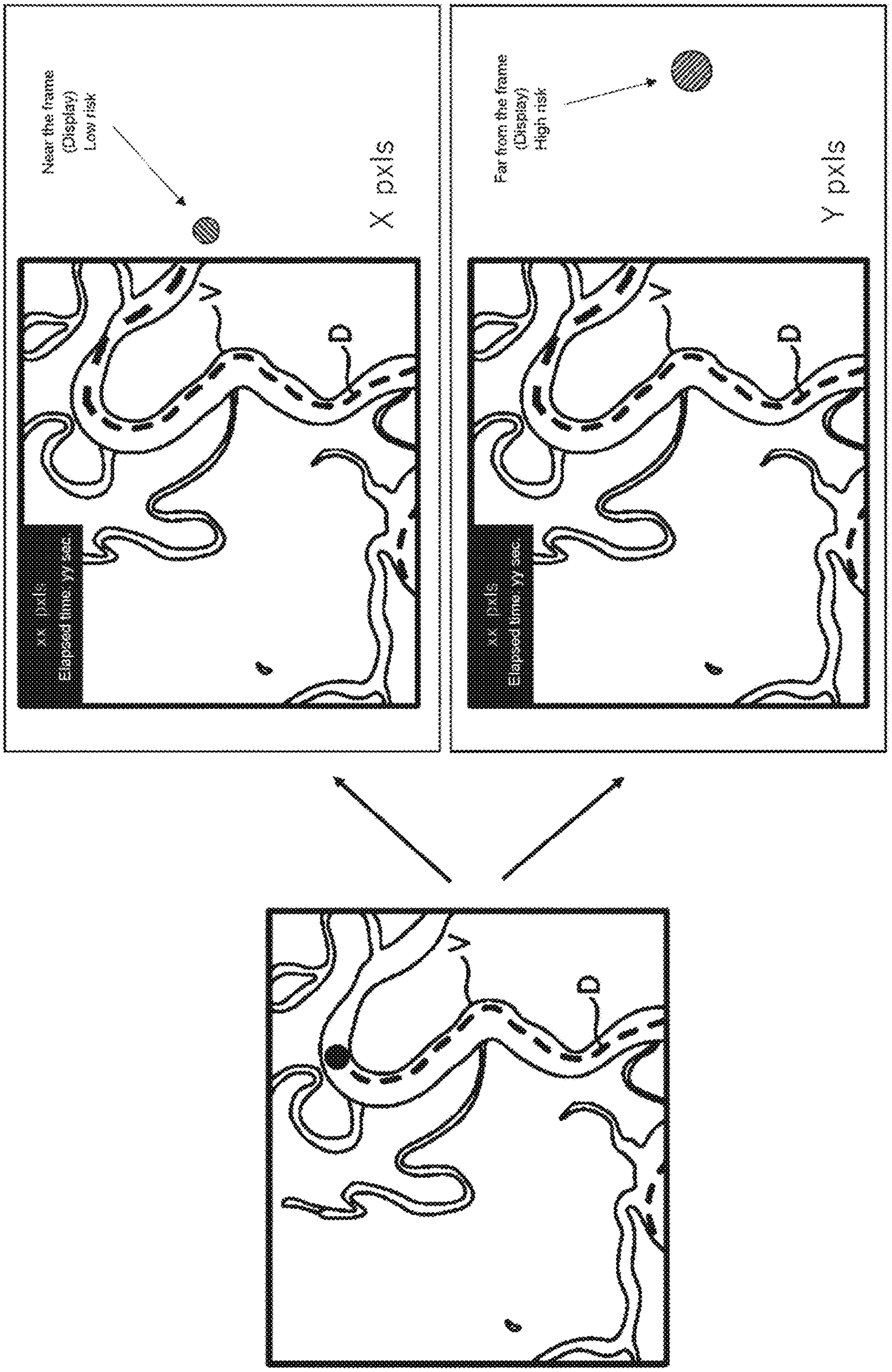
FIG. 16 It is a figure for demonstrating an example of the display of the estimation result of the status estimation unit according to the embodiment.

In addition, some embodiments of the present invention relate to a device that calculates the level of risk from the estimated state and issues a notification to the user according to the level of risk. The position, speed, and risk level of the region of interest estimated by the status estimation unit can be displayed on a display device. The display method can be, but is not limited to, display by a point, an arrow, or a heat map. For example, if the position of the estimated region of interest is more than a predetermined distance from the edge of the image, it can be determined to be at high risk (FIG. 16). For example, in FIG. 16, the position of the estimated region of interest is indicated by a circle, and the further away from the edge of the screen the position is estimated to be, the higher the level of risk is judged to be. In this case, for example, the risk level may be indicated by the color of the circle (for example, green is low risk level and red is high risk level). If the calculated level of risk exceeds a certain threshold, an alert can be displayed on the screen of the display device. Or, an audio notification may be provided in addition.

Accordingly, some embodiments of the present invention relate to an image processing apparatus, which is an image processing apparatus comprising an image acquisition unit for acquiring an image including at least a device for examination or treatment in a blood vessel as a photographic subject, a region of interest acquisition unit for acquiring one or more regions in the image that include at least a portion of the device as a region of interest, a tracking unit that tracks each of the regions of interest in the image, and a notification unit that notifies the user of the image processing apparatus when a region including the tip portion of a catheter or the tip portion of a guide wire is set as the region of interest, on the condition that the region of interest disappears from the image, and a status estimation unit that estimates the current position and/or speed of the tip portion of the catheter or the tip portion of the guide wire based on the position, speed and/or speed of the tip portion of the catheter or the tip portion of the guide wire immediately before the region of interest disappears from the image, wherein a warning is issued to the user when the current position and/or speed of the region of interest estimated by the status estimation unit exceeds a predetermined threshold value.

Some embodiments of the present invention relate to a program for executing the above method on a computer. Some embodiments of the present invention also relate to an image processing apparatus for executing the above methods and a method for operating the same.

<Processing Flow of Estimating the Position of the Region of Interest Outside the Frame>

Figure 24:
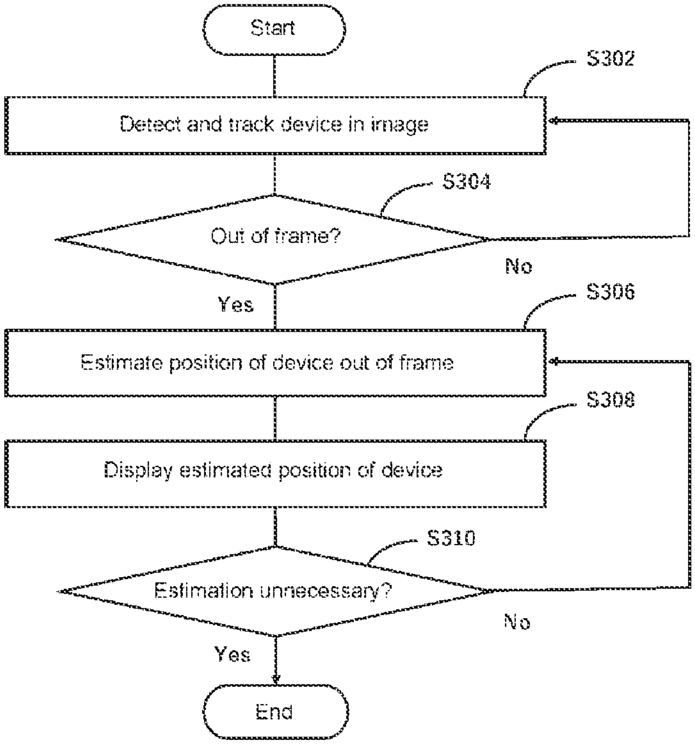
FIG. 24 It is a flowchart for demonstrating the flow of the processing of estimating the position of the region of interest outside the frame executed by the image processing apparatus according to the embodiment.

FIG. 24 is a flowchart for explaining the processing flow of estimating the position of the region of interest outside the frame, which is executed by the image processing apparatus according to the embodiment. The processing in this flowchart starts, for example, when the image processing apparatus 1 is started.

First, the image acquisition unit 110, region of interest acquisition unit 111, and tracking unit 112 function to detect and track the device D for examination or treatment in the blood vessel V by video analysis (S302).

Next, it is determined as to whether the site of the device D to be notified has gone outside the frame of the screen (S304) or not, and if the condition is met, the location of the device outside the frame is estimated (S306). For example, the position of the device D outside the frame is inferred from the front side of the black part of the guide wire, filter, balloon, or such, which is visible on the screen connected to the device D. The estimation can be done by using the difference in distance, machine learning, or such.

Next, the estimated position of the device is displayed (S308). The estimated position of the device D outside the frame is displayed on the display screen as the actual estimated position or distance from the frame. The further out of the frame, the stronger the display or notification may be.

Finally, whether the estimation is no longer necessary or not is determined based on the reason that the device D has returned to the inside of the frame of the screen, or that the user (surgeon/assistant) has pressed a button that does not require display (S310). After this is completed, processing in this flowchart may be started again.

(Layout and Notification)

In some embodiments of the present invention, the results of image analysis can be displayed on two screens of different sizes. As mentioned above, endovascular surgery is generally performed while viewing multiple screens (for example, four screens), and the surgeon can grasp three-dimensional information by viewing at least two screens (generally, frontal (AP or F direction: Anterior-Posterior, Frontal) and lateral (R L or LAT direction: Right to Left, Lateral). Therefore, it is important to display both frontal and lateral images, and it is very important to display them in an easily viewable manner on a monitor of limited physical size. In actual surgery, monitors are often placed over the patient's bed at a distance of 1 m or more, and instructions are often given to bring the monitor as close as 1 cm to the surgeon. The frontal and lateral views are always viewed from an angle that moves three-dimensionally, for example, 15 degrees to the right and 10 degrees to the head side using the frontal tube. In this way, even when three dimensions are projected onto two dimensions, they are viewed at an angle so that they can be seen clearly even in two dimensions. Furthermore, in the case of four screens, there are the frontal Live and Mask and the lateral Live and Mask. Live is a normal fluoroscopic image, similar to a typical radiograph, which is viewed in real time. Mask is the difference (subtraction) from any arbitrary previous Live image selected by the surgeon. As a result, the bones that were visible in Live disappear, and for example, only the blood vessels and devices that are shown by the contrast medium can be seen, and an image that is easy for the surgeon to understand can be obtained.

Figure 18:
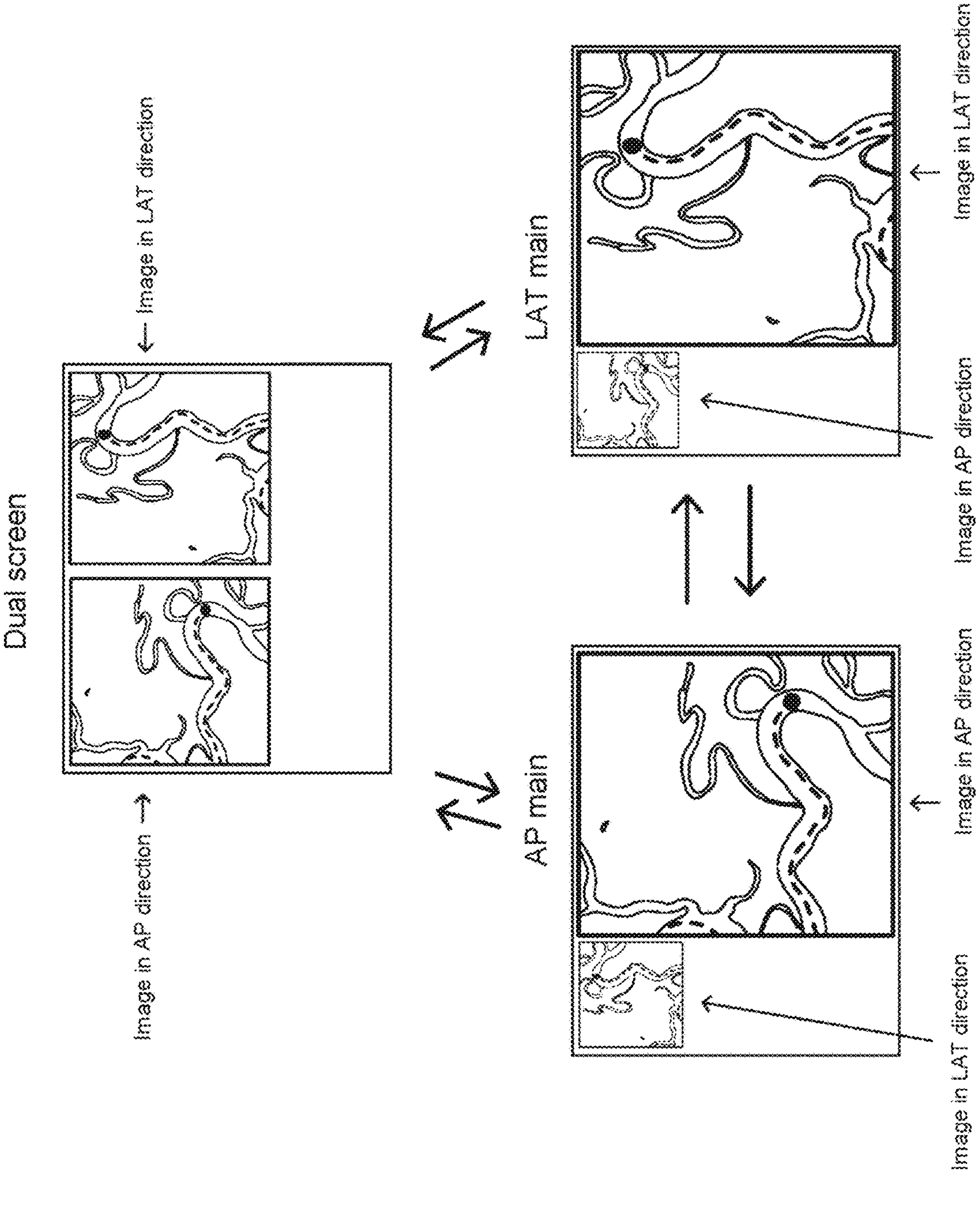
FIG. 18 It is a figure for demonstrating an embodiment which displays the result of image analysis on two screens of different sizes.

The two screens of different sizes can be switched automatically or by selection of the user (surgeon) (see FIG. 18). Since there are physical limits to the screen size and one may want to see one of the screens larger than the other, visibility can be improved by displaying the two screens in different sizes, as shown in FIG. 18.

Figure 19:
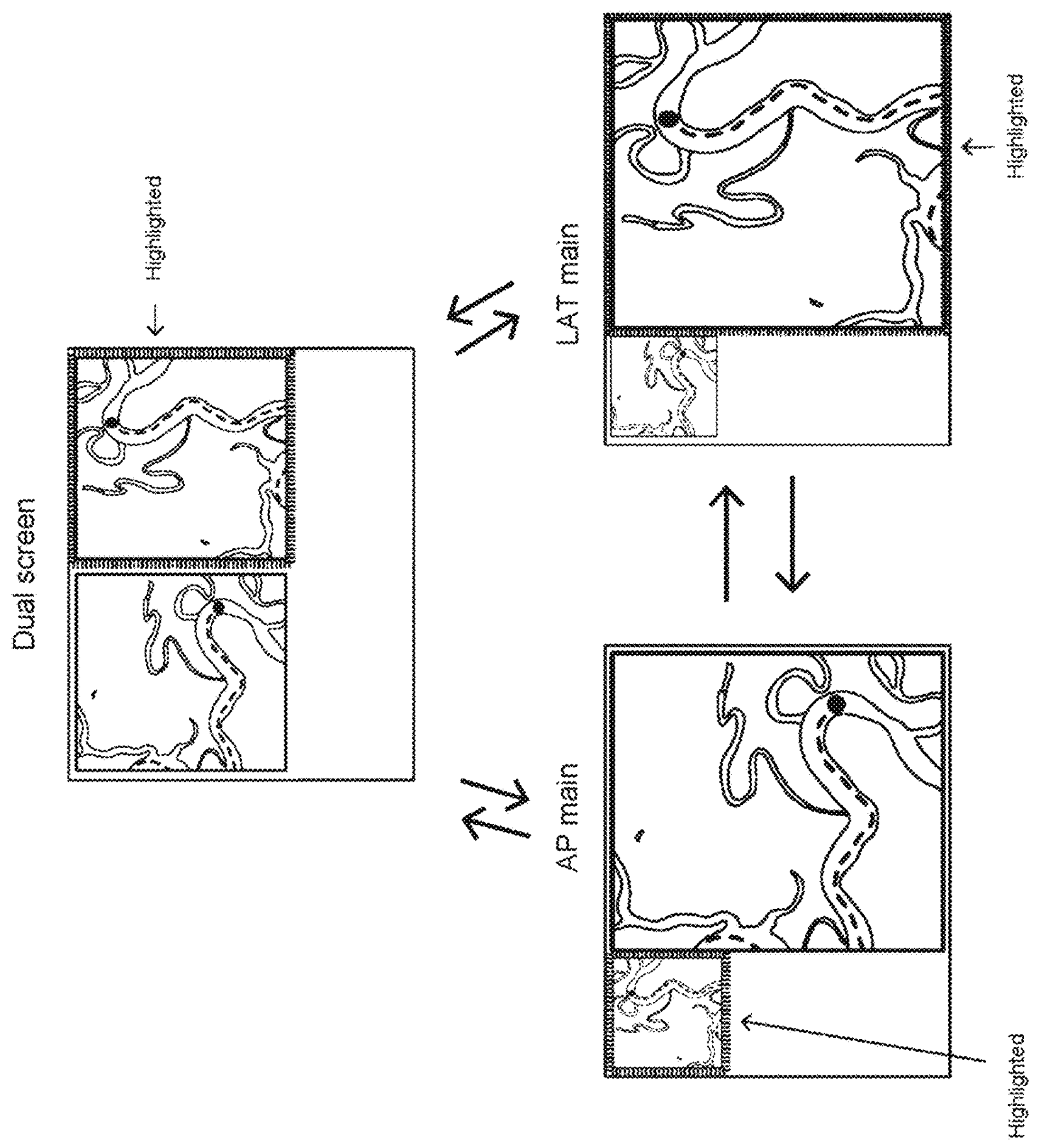
FIG. 19 It is a figure for demonstrating an embodiment which recognizes a screen to be notified by highlighting the frame of the screen.

In addition, the screen to be notified can be recognized by the user by making the frame portion of the screen glow, changing the color, or highlighting the screen (see FIG. 19). As shown in FIG. 19, notifications with colored frames or such make it easier for the user to know which screen to pay attention to. If the notification is issued on the side of the smaller screen, the two screens may be automatically switched (thereby switching the area of attention to a larger, easier-to-see screen). As such, in some embodiments of the present invention, the display device may be equipped with a function to alert the user by making the frame portion of one of the two screens glow, changing the color, or highlighting the screen.

(Probability-Based Display)

In some embodiments of the present invention, the region of interest in the screen is output as a probability distribution, so the presence of the region of interest can be expressed in terms of probability. The probability distribution of the region of interest that exists can be displayed as a numerical value, color, bar, or such. In addition, it is also possible to express the probability of whether or not a scene should be notified. Whether or not a scene should be notified can be displayed as a numerical value, color, bar, or such, depending on the probability. It is also possible to display which part of the screen is the responsible part as a probability distribution by means of a heat map or such.

The probability distribution may be converted and displayed in a way that is easy to understand. For example, 0-30% may be displayed as low, 30-70% as middle, and 70-100% as high in text or displayed in three colors. As another example, the area below 70% may be slightly darkened so that the region of interest or the region to be notified appears bright like a spotlight.

Thus, in some embodiments of the present invention, the notification unit can display an image on a display device by a numerical value, color, bar or heat map according to the probability that at least one of the regions of interest satisfies a condition defined for each of the regions of interest, or a numerical value, color, bar or heat map based on any transformation applied to the probability distribution. Further, the notification unit can color the region of interest with a color or heat map according to the probability that at least one of the regions of interest satisfies a condition defined for each of the regions of interest, or with a color or heat map based on an arbitrarily transformed value of the probability distribution, and display it on the display device displaying the image. Alternatively, it can also replace the probability that satisfies a condition with a numerical value or color and display it on the display device displaying the image.

(Device Selection Display and Recording)

There are a variety of devices used in endovascular therapy, and many different types exist for each of them. Examples of devices include various catheters, catheters with balloons, guide wires, stents, flow-diverting stents (stents with fine mesh), coils, embolic materials (materials such as liquids or particles), and other embolic devices (such as WEB). Further, in each of these devices, there are also various types. For example, in catheters, there are standards for the tip shape, length, lumen, outer lumen, hardness and such. For coils, hundreds of types exist, and there are standards for the manufacturer, thickness, total length, diameter, hardness, and such. It is impossible to memorize all of these, and it is also impossible to know what is in stock, so the surgeon checks with the vendor during the procedure. The combination of coils is also important, and the size of the coils is determined by looking at the images. Since 5 to 15 coils are usually used for an aneurysm, it is necessary to consider which coil to use next, but it is difficult for surgeons and assistants to remember the inventory management, lineups and such. Because new products are introduced and old products are discontinued, it is difficult to keep track of the situation, and the available lineups vary from facility to facility. At present, the selection of devices is made through communication with vendors during treatment, but this is not smooth.

First, a database of the lineup and standards of devices currently available in the country should be created. Inventory information at each facility can also be included. A system that displays this information on a monitor is built. For example, when a microcatheter is selected, the available microcatheter lineups, standards, inventory information and such are listed up and displayed. As additional information, it is also possible to search information on whether the guiding catheter can accommodate that device or multiple devices. For example, if the lumen of a guiding catheter is R and the outer diameters of two devices are r1 and r2, the two devices will fit inside the guiding catheter if $R>r1+r2$. The same idea can be applied to one device or three or more devices.

As another example, in the case of coils, the choice of coil lineups (length, diameter, hardness, shape, or such) is based on the size of the aneurysm and the behavior of the previously placed coil. There are several hundred types of coil lineups, but by specifying the length and such, it is easy to make a list. By displaying them on the monitor, it is easier to make a selection during treatment. Since most coil selections are made with the same or smaller diameters and lengths, the lineup of coils that are most likely to be used can be presented based on the information of coils used up to that point. Presentations that take inventory into consideration can also be made. In addition, lineup candidates can include preferences based on the facility and surgeon (user). Suggestions can be made based on the aneurysm or coil winding method based on image analysis. The surgeon selects the desired device from such a list and performs the surgery. This information is recorded and can be used to automatically create a surgical record, for example, in combination with snapshots of the treatment video.

Figure 20:
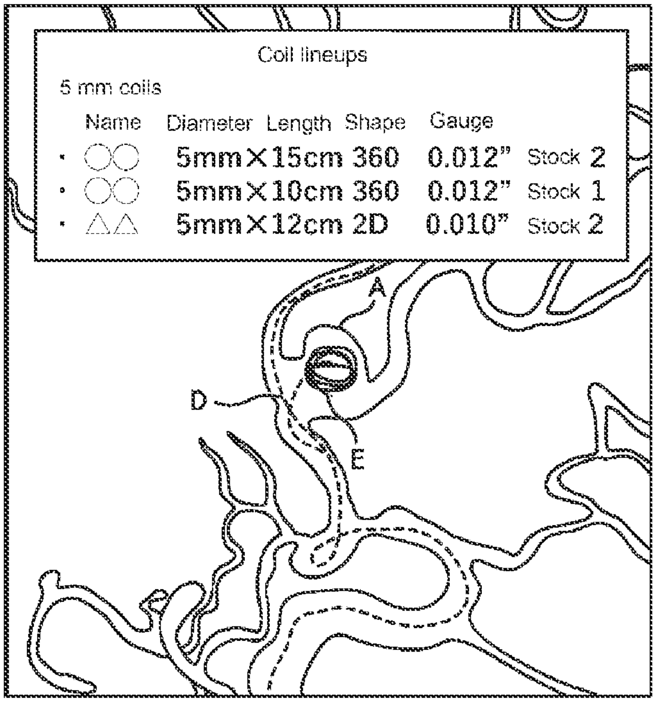
FIG. 20 It is a figure for demonstrating a display of the product list of the devices (for example, various types of catheters and coils) for examination or treatment in blood vessels according to the embodiment.

In some embodiments of the present invention, the display device that displays the image can display a product list of devices (for example, various types of catheters and coils) for examination or treatment in the blood vessel (see FIG. 20). Further, the display device may also display a product list narrowed down by size or inventory. In addition, the display device may show a list of recommended products based on results of image analysis, facility information, or user preference information.

In some embodiments of the present invention, the image processing apparatus may automatically or based on the user selection create a surgical record that includes information about the device used, the images acquired, and the image analysis results.

Thus, some embodiments of the present invention also relate to a system, which is an endovascular surgical support system that includes a storage unit which stores a product list of devices (for example, various catheters and coils) for examination or treatment in a blood vessel, a recommendation unit that recommends products for use based on image analysis results, facility information, or user preference information, and a display unit that displays the recommended products.

Exemplary System

Some embodiments of the present invention relate to vascular catheterization support systems, for example, catheterization support systems for cerebral, cardiac, peripheral limbs, and abdominal vessels, in particular, cerebral blood vessels. Such a system is a system that can comprise an image processing apparatus and an image capture device that captures and transmits to the image processing apparatus X-ray images of a patient with one or more devices inserted into a blood vessel, wherein the image processing apparatus is equipped with an image acquisition unit that acquires X-ray images over time of a region (for example, a fixed region) that includes at least an area of interest for achieving a surgical objective and a device inserted into a blood vessel, a region of interest acquisition unit that acquires one or more regions which include at least a portion of the device included in the image as a region of interest, a tracking unit that tracks each of the regions of interest in the image, and a notification unit that notifies a user of the image processing apparatus when at least one of the regions of interest meets a condition defined for each of the regions of interest, wherein one or more of the devices are a catheter, guide wire, stent and/or balloon, and a region including the tip portion of a catheter or the tip portion of a guide wire, both ends of the stent, and both ends of the balloon is set as the region of interest, and the user is notified on the condition that the region of interest disappears from the image, the distance between the region of interest and the edge of the image is less than a predetermined threshold distance, or that the region of interest has shifted a certain distance.

Here, the notification unit may display the distance between the region of interest and the edge of the image or the distance between the marker and the region of interest on a display device that displays the image, and the notification unit can change the manner in which the distance is displayed on the display device according to the length of the distance, and the change in the display mode may include changing the font, size, or color of the characters displayed according to the length of the distance, changing the color of the entire screen or a portion of the screen of the display device according to the length of the distance, displaying a graphic on the entire screen or outside the frame of the display device or in a part of the screen, enlarging and displaying the region of interest according to the length of the distance, or changing the color or size of the mark attached to the region of interest according to the length of the distance. The notification unit may also sound a notification tone in accordance with the length of the distance. Furthermore, the distance may be determined by either a straight line distance or a distance along a blood vessel.

Some embodiments of the present invention also relate to an aneurysm coil embolization assistance system, in particular, a cerebral aneurysm coil embolization assistance system. Such a system is a system that can be equipped with an image processing apparatus and an image capture device that captures and transmits to the image processing apparatus X-ray images of a patient in a state with a guiding catheter and a delivery wire for an embolic coil inserted into a blood vessel, wherein the image processing apparatus is equipped with an image acquisition unit that acquires X-ray images over time of a fixed area that includes at least the aneurysm in the patient's blood vessel, a catheter inserted into the blood vessel and a delivery wire for an embolization coil, a region of interest acquisition unit that acquires one or more areas that include at least a portion of the guiding catheter in the images as a region of interest, a marker detection unit that detects a marker provided on the delivery wire, which is a marker that approaches one or more regions of interest set in a portion of the catheter guiding the delivery wire, a tracking unit that tracks each of the regions of interest and the markers in the images, and a notification unit that notifies the user of the timing when the embolic coil may be detached from the delivery wire, triggered by the superimposition of the marker and the region of interest.

Here, the notification unit may display the distance between the region of interest and the edge of the image or the distance between the marker and the region of interest on a display device that displays the image, and the notification unit can change the manner in which the distance is displayed on the display device according to the length of the distance, and the change in the display mode may include changing the font, size, or color of the characters displayed according to the length of the distance, changing the color of the entire screen or a portion of the screen of the display device according to the length of the distance, displaying a graphic on the entire screen or outside the frame of the display device or in a part of the screen, enlarging and displaying the region of interest according to the length of the distance, or changing the color or size of the mark attached to the region of interest according to the length of the distance. The notification unit may also sound a notification tone in accordance with the length of the distance. Furthermore, the distance may be determined by either a straight line distance or a distance along a blood vessel.

<Processing Flow of the Image Processing Method Executed by the Image Processing Apparatus 1>

Figure 10:
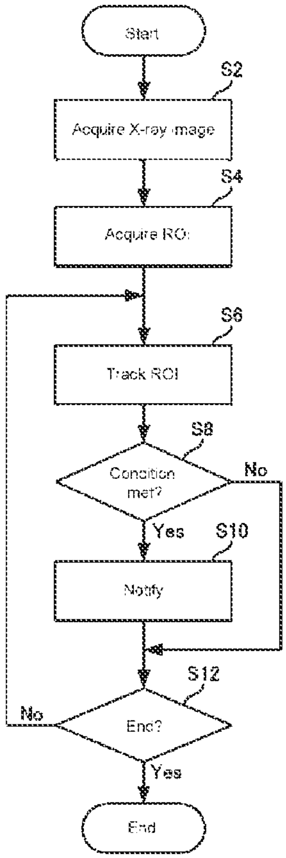
FIG. 10 It is a flowchart for demonstrating the flow of the image analysis processing executed by the image processing apparatus according to the embodiment.

FIG. 10 is a flowchart illustrating the flow of the image analysis processing performed by the image processing apparatus 1. The processing in this flowchart starts, for example, when the image processing apparatus 1 is started.

The image acquisition unit 110 acquires an X-ray image created based on the absorption rate of X-rays, which includes at least a blood vessel V and a device D for examination or treatment in the blood vessel Vas a photographic subject (S2). The region-of-interest acquisition unit 111 acquires one or more regions including at least a portion of the device D in the X-ray image as the region-of-interest R (S4).

The tracking unit 112 tracks each of the regions of interest R in the X-ray image (S6). If at least one of the regions of interest R satisfies a condition defined for each of the regions of interest R (Yes in S8), the notification unit 113 notifies the user of the image processing apparatus 1 of that fact (S10). If all the regions of interest R fail to satisfy the defined condition (No in S8), the notification unit 113 skips the notification processing.

Until the image processing is completed (No in S12), the image processing apparatus 1 returns to step S6 and repeats the processing from step S6 to step S10. When the image processing is completed (Yes in S12), the processing in this flowchart is terminated.

<Diagnosis and Comparison of Angiography>

In angiographic examination and treatment, blood vessels are visualized by contrast imaging to diagnose lesions, but sometimes the images are overlooked or must be judged by comparing them with images taken the same day before or on a different day, which can be time-consuming and difficult to compare. In addition, since the images are projected in two dimensions, it can be difficult to make a judgment. Therefore, some embodiments of the present invention relate to an image diagnosis device that points out lesions or sites of lesion including, without limitations thereto, cerebral aneurysm, stenosis, occlusion, thrombus formation, vascular perforation (spillage of the contrast medium), shunt disease, nutrient vessel and tumor thickening of tumor vessels, venous thrombosis, avascular area of the capillary phase (finding of vascular occlusion), collateral circulation, and such, as determined by deep learning and other methods used in contrast-enhanced angiography. Thus, in some embodiments of the present invention, the image processing apparatus can further comprise a lesion recognition unit that recognizes a lesion selected from the group consisting of aneurysm, stenosis, vasospasm, dissection, occlusion, recanalization, thrombosis, site of thrombus and location of both ends, vascular perforation, leakage of contrast medium out of a blood vessel, calcification of a blood vessel, arteriosclerosis, shunt disease and its feeding and draining vessels, blood (contrast medium) backflow, and cerebral arteriovenous malformations, dural arteriovenous fistulas, avascular region, bony merkmals (internal auditory canal, ocular fundus, supraorbital margin, pyramidal body, foramen magnum occipitalis, cervical spine, clavicle, rib and spine numbers, femoral head, pelvis), feeding vessels of tumor and tumor staining, venous occlusion, venous sinus thrombosis, avascular area of capillary phase, vascular occlusion, coil shape and distribution within the aneurysm, balloon position, inflation, and shape, coil deviation into the normal vessel, insufficient expansion of stent, degree of adherence to the vessel and torsion of stent, stent migration, positional relationship between puncture site and blood vessel (no stenosis, none near bifurcation), vessel tortuosity, type of aortic arch (how far down from the top of the aortic arch the right brachiocephalic artery is), extent of penetration of liquid embolic material, delay or stagnation of blood (contrast medium) flow, blood vessel variations (anterior communicating artery, anterior cerebral artery A1, posterior communicating artery, posterior cerebral artery P1, posterior inferior cerebellar artery, anterior inferior cerebellar artery, superior cerebellar artery, superficial temporal artery, presence and development of each venous sinus and each venous vein), moyamoya vessels of moyamoya disease (stenosis and occlusion of the tip of the internal carotid artery and development of collateral vessels beyond it), location of arterial bifurcations and segments (internal carotid artery conus, cavernous sinus, ophthalmic artery, middle cerebral artery M1 bifurcation), past surgery devices (clips, coils, plates, shunt tubes/valves, ventricular tubes and cistern tubes), position/openness of WEB devices, foreign bodies (dentures, plates), and collateral circulation in the said images. The system may not go so far as to point out the lesion, but may notify when an abnormal finding is suspected, or point out which areas in the region may be abnormal. In such cases, the physician can make the final decision. Similarly, some embodiments of the present invention relate to an image diagnosis device that points out changes in performing imaging of a blood vessel, when comparing with the previous imaging or imaging performed on a different day. Thus, in some embodiments of the present invention, the image processing apparatus can further comprise an image recognition unit that compares the angiographic image in the image with a previously acquired and stored angiographic image and notifies the change. For example, changes in the degree of vasospasm, changes in thrombus formation (appearance, disappearance, enlargement, reduction, or such), release of occluded vessels, vessel occlusion, coil deviation, stent movement, or such can be noted.

<Effects of the Image Processing Apparatus 1 According to the Embodiment>

As explained above, the image processing apparatus 1 according to the embodiment can provide technology to support judgment of the area of interest in catheter examination or treatment of blood vessels by allowing the user, a medical professional, to concentrate on the work in the area of interest.

Although the present invention has been described above using the embodiments, the technical scope of the invention is not limited to the scope described in the above embodiments, and various variations and modifications are possible within the gist thereof. For example, all or part of the device can be functionally or physically distributed or integrated in any arbitrary unit. New embodiments resulting from any combination of multiple embodiments are also included in the present invention. The effects of a new embodiment created by the combination have the effect of the original embodiment.

Example of a First Modification

In the above, the examination and treatment of cerebral blood vessels were mainly described. However, the applicable subject of the present invention is not limited to the cerebrovascular system, but can be applied to examination and treatment of blood vessels including the circulatory system such as the heart, peripheral limbs, abdomen and such.

Example of a Second Modification

In the above, the explanation was given using the example of a device with two screens as shown in FIGS. 7(*a*)-(*b*), but the number of screens is not limited to this, and for example, it can be one screen, or three screens or more.

Example of a Third Modification

In the above, the case in which the X-ray imaging apparatus 3 captures images of the surgical site of the test subject P was explained. However, the imaging apparatus for capturing images of the test subject P's surgical site is not limited to the X-ray imaging apparatus 3. Other modalities such as MRI (Magnetic Resonance Imaging) and ultrasonography may also be used to capture images of the surgical site.

Examples of the Embodiments

Some or all of the above embodiments may also be described in the Supplementary Notes below, but the disclosure of this application is not limited to the following Supplementary Notes

Supplementary Note 1

An image processing apparatus, comprising: an image acquisition unit for acquiring an image including at least a device for examination or treatment in a blood vessel as a photographic subject, a region of interest acquisition unit for acquiring one or more regions in the image that include at least a portion of the device as a region of interest, a tracking unit that tracks each of the regions of interest in the image, and a notification unit that notifies the user of the image processing apparatus when at least one of the interest regions satisfies a condition determined for each of the regions of interest.

Supplementary Note 2

The image processing apparatus according to Supplementary Note 1, wherein the notification unit notifies the user when a region including the tip portion of a catheter or the tip portion of a guide wire is set as the region of interest, on the condition that the region of interest disappears from the image.

Supplementary Note 3

The image processing apparatus according to Supplementary Note 1, wherein the notification unit notifies the user when a region including the tip portion of a catheter or the tip portion of a guide wire is set as the region of interest, on the condition that the distance between the region of interest and the edge of the image is less than a predetermined threshold distance.

Supplementary Note 4

The image processing apparatus according to any one of Supplementary Notes 1 to 3, wherein the notification unit notifies the user on the condition that at least one of the movement distance, the movement speed, and the acceleration of the region of interest in the image exceeds a predetermined threshold value.

Supplementary Note 5

The image processing apparatus according to any one of Supplementary Notes 1 to 4, wherein the notification unit displays the distance between the region of interest and the edge portion of the image on a display device for displaying the image.

Supplementary Note 6

The image processing apparatus according to Supplementary Note 5, wherein the notification unit changes the display mode of the distance in the display device according to the length of the distance between the region of interest and the edge portion of the image.

Supplementary Note 7

The image processing apparatus according to any one of Supplementary Notes 1 to 6, wherein the notification unit notifies the user on the condition that the value obtained by dividing the distance between the region of interest and the edge of the image by the movement speed of the region of interest in the image is less than a predetermined threshold value.

Supplementary Note 8

The image processing apparatus according to any one of Supplementary Notes 1 to 6, which is further equipped with a marker detection unit that detects a marker established on the delivery wire of the embolic coil that approaches a region of interest configured in a portion of the microcatheter that guides the delivery wire, wherein the tracking unit further tracks the detected marker, and the notification unit notifies the user when the embolic coil may be detached from the delivery wire, as triggered by the superimposition of the marker and the region of interest.

Supplementary Note 9

The image processing apparatus according to Supplementary Note 8, wherein the notification unit notifies the user when the marker has passed through the region of interest.

Supplementary Note 10

The image processing apparatus according to Supplementary Note 8 or 9, wherein the notification unit displays on the display device the distance that the marker should move before detaching the embolic coil from the delivery wire.

Supplementary Note 11

The image processing apparatus according to any one of Supplementary Notes 1 to 10, wherein a feature value indicating the shape of the device included in the region of interest satisfies a predetermined condition, the notification unit notifies the user of the image processing apparatus of this fact.

Supplementary Note 12

The image processing apparatus according to Supplementary Note 11, wherein the feature value is a curvature, and the notification unit notifies the user of the device included in the region of interest on the condition that the curvature of the device exceeds a predetermined threshold curvature or that the curvature is changing but the tip is not moving.

Supplementary Note 13

The image processing apparatus according to Supplementary Note 11 or 12, wherein the notification unit notifies the user on the condition that the length of the device in the image or region of interest minus the length of the centerline of the blood vessel in the image or region of interest exceeds a predetermined threshold length.

Supplementary Note 14

The image processing apparatus according to any one of Supplementary Notes 1 to 13, wherein the notification unit notifies the user by coloring the region of interest with a different color from the image, changing the font, size, or color of the characters displayed, changing the color of the entire screen or part of the screen of the display device, displaying a graphic on the entire screen, outside the frame, or in some other location of the display device, enlarging the region of interest, or changing the color or size of a mark attached to the region of interest.

Supplementary Note 15

The image processing apparatus according to any one of Supplementary Notes 1 to 14, wherein the notification unit notifies the user when a region including the tip portion of the catheter or the tip portion of the guide wire is set as the region of interest, on the condition that the region of interest has moved, or the region of interest exceeds a specific range specified on the image.

Supplementary Note 16

The image processing apparatus according to any one of Supplementary Notes 1 to 15, further comprising an image storage unit for storing an image or a video obtained from an image acquisition unit over time.

Supplementary Note 17

The image processing apparatus according to Supplementary Note 16, further comprising an image extraction unit that extracts video images from the image storage unit for a certain period of time before and after the notification is issued by the notification unit, or at any time point or any period of time specified by the user.

Supplementary Note 18

The image processing apparatus according to Supplementary Note 17, wherein the image extraction period is automatically determined based on at least one of the movement distance, the movement speed, and the acceleration of the region of interest when the notification occurs.

Supplementary Note 19

The image processing apparatus according to Supplementary Note 17 or 18, wherein the extracted video is displayed on a display device.

Supplementary Note 20

The image processing apparatus according to Supplementary Note 19, wherein the extracted video is automatically and repeatedly displayed a predetermined number of times.

Supplementary Note 21

The image processing apparatus according to Supplementary Note 20, wherein the extracted video is displayed based on any arbitrary operation including playback, stop, fast forward, rewind, frame advance, slow playback, and double-speed playback.

Supplementary Note 22

The image processing apparatus according to any one of Supplementary Notes 17 to 21, wherein the time elapsed from the time when the notification occurred, a comparison of the position of the region of interest at the time when the notification occurred and after any arbitrary elapsed time, or the trajectory of the region of interest obtained by the tracking unit is superimposed on the extracted image and further displayed.

Supplementary Note 23

The image processing apparatus according to any one of Supplementary Notes 17 to 21, wherein the extracted video is displayed by cutting out a portion of an area in the vicinity of the region of interest.

Supplementary Note 24

The image processing apparatus according to any one of Supplementary note 17 to 23, wherein the extracted video is displayed at a position that does not interfere with the display of the region of interest.

Supplementary Note 25

The image processing apparatus according to any one of Supplementary Notes 17 to 24, wherein the extracted video is enlarged and displayed.

Supplementary Note 26

The image processing apparatus according to any one of Supplementary Notes 17 to 25, wherein the extracted video is displayed at the same time as the occurrence of the notification or after a predetermined time has elapsed from the occurrence of the notification.

Supplementary Note 27

The image processing apparatus according to any one of Supplementary Notes 17 to 26, wherein images taken from multiple directions are simultaneously displayed.

Supplementary Note 28

The image processing apparatus according to any one of Supplementary Notes 2 to 27, which is further equipped with a status estimation unit that estimates the current position and/or speed of the tip portion of the catheter or the tip portion of the guide wire that has disappeared from the image based on the position, speed and/or acceleration of the tip portion of the catheter or the tip portion of the guide wire immediately before the region of interest disappears from the image.

Supplementary Note 29

The image processing apparatus according to Supplementary Note 28, wherein a warning is issued to the user when the current position and/or speed of the region of interest estimated by the status estimation unit exceeds a predetermined threshold value.

Supplementary Note 30

The image processing apparatus according to any one of Supplementary Notes 1 to 29, wherein the display device displaying the image displays two images on two screens of different sizes.

Supplementary Note 31

The image processing apparatus according to Supplementary Note 30, wherein the display device calls attention to the user by making the frame portion of one of the two screens glow, changing the color, or highlighting the screen.

Supplementary Note 32

The image processing apparatus according to any one of Supplementary Notes 1 to 31, wherein the display device displaying the image displays a product list of devices for endovascular examination or treatment.

Supplementary Note 33

The image processing apparatus according to Supplementary Note 32, wherein the display device displays a list of products narrowed down by size or inventory.

Supplementary Note 34

The image processing apparatus according to Supplementary Note 32 or 33, wherein the display device displays a list of recommended products based on a result of image analysis, facility information, or user preference information.

Supplementary Note 35

The image processing apparatus according to any one of Supplementary Notes 1 to 34, which automatically or based on the user selection creates a surgical record that includes information of the device used, information of the images acquired, and a result of the image analysis.

Supplementary Note 36

The image processing apparatus according to any one of Supplementary Notes 1 to 35, wherein the notification unit displays on a display device a numerical value, color, bar or heat map according to the probability that at least one of the regions of interest satisfies a condition defined for each of the regions of interest, or a numerical value, color, bar or heat map based on any transformation applied to the probability distribution.

Supplementary Note 37

The image processing apparatus according to any one of Supplementary Notes 1 to 35, wherein the notification unit colors the region of interest with a color or heat map according to the probability that at least one of the regions of interest satisfies a condition defined for each of the regions of interest, or with a color or heat map based on an arbitrarily transformed value of the probability distribution, and displays it on the display device displaying the image, or alternatively, replaces the probability that satisfies the condition with a numerical value or color and displays it on the display device displaying the image.

Supplementary Note 38

The image processing apparatus according to any one of Supplementary Notes 1 to 37, wherein the notification unit notifies the user when a region including the tip portion of the catheter or the tip portion of the guide wire is set as the region of interest, on the condition that the region of interest has moved, or the region of interest exceeds a specific range specified on the image.

Supplementary Note 39

The image processing apparatus according to Supplementary Note 38, wherein the boundary line of the specific range is represented by a straight line, a curve, a circle, a rectangle, or any other polygon.

Supplementary Note 40

The image processing apparatus according to Supplementary Note 38 or 39, wherein the specific range is superimposed and displayed on an X-ray image.

Supplementary Note 41

The image processing according to any one of Supplementary Notes 38 to 40, wherein the notification unit displays the distance between the region of interest and the edge portion of the specific range on a display device displaying the image.

Supplementary Note 42

The image processing according to Supplementary Note 41, wherein the notification unit changes the display mode of the distance in the display device according to the length of the distance between the region of interest and the edge portion of the specific range.

Supplementary Note 43

The image processing according to any one of Supplementary Notes 38 to 40, wherein the notification unit notifies the user on the condition that the value obtained by dividing the distance between the region of interest and the edge of the specific range by the movement speed of the region of interest in the image is less than a predetermined threshold value.

Supplementary note 44

The image processing apparatus according to any one of Supplementary Notes 3 to 43, wherein the distance is determined by either a straight line distance or a distance along a blood vessel.

Supplementary Note 45

The image processing apparatus according to any one of Supplementary Notes 1 to 44, comprising a storage unit that acquires and stores the position and/or shape of a device for examination or treatment in a blood vessel at any point in time, wherein the stored device position and/or shape are superimposed on images since the acquisition.

Supplementary Note 46

The image processing apparatus according to any one of Supplementary Notes 1 to 42, further comprising a lesion recognition unit that recognizes a lesion selected from the group consisting of cerebral aneurysm, stenosis, occlusion, thrombus formation, vascular perforation, spillage of the contrast medium, shunt disease, nutrient vessel and tumor thickening of tumor vessels, venous thrombosis, avascular area of the capillary phase, vascular occlusion, and collateral circulation in the image.

Supplementary Note 47

The image processing apparatus according to any one of Supplementary Notes 1 to 43, further comprising an image recognition unit that compares the angiographic image in the image with a previously acquired and stored angiographic image and notifies the change.

Supplementary Note 48

An image processing method, in which a processor of an image processing apparatus performs a step of acquiring an image that includes at least a device for examination or treatment in a blood vessel as a photographic subject; a step of acquiring one or more regions that include at least a portion of the device in the image as a region of interest; a step of tracking each of the regions of interest in the image; and a step of notifying a user of the image processing apparatus when at least one of the regions of interest satisfies a condition defined for each of the regions of interest.

Supplementary Note 49

A program that realizes on a computer, a function of acquiring an image that includes at least a device for examination or treatment in a blood vessel as a photographic subject, a function of acquiring one or more regions that include at least a portion of the device in the X-ray image as a region of interest, and a function of tracking each of the regions of interest in the X-ray image, and a function of notifying a user of the computer when at least one of the regions of interest satisfies a condition defined for each of the regions of interest.

Supplementary Note 50

An image processing system, which is equipped with the image processing apparatus according to any one of Supplementary Notes 1 to 44 and an imaging apparatus that captures an image of a person in a state in which a device for examination or treatment in a blood vessel is inserted and transmits the image to the image processing apparatus Supplementary Note 51

A cerebrovascular catheterization surgery support system, which is a system equipped with an image processing apparatus and an image capture device that captures and transmits to the image processing apparatus X-ray images of a patient with one or more devices inserted into a blood vessel, wherein the image processing apparatus is equipped with an image acquisition unit that acquires X-ray images over time of a fixed region that includes at least an area of interest for achieving a surgical objective and a device inserted into a blood vessel, a region of interest acquisition unit that acquires one or more regions which include at least a portion of the device included in the image as a region of interest, a tracking unit that tracks each of the regions of interest in the image, and a notification unit that notifies a user of the image processing apparatus when at least one of the regions of interest meets a condition defined for each of the regions of interest, wherein one or more of the devices are a catheter, guide wire, stent and/or balloon, and wherein a region including the tip portion of the catheter or the tip portion of the guide wire, both ends of the stent, and both ends of the balloon is set as the region of interest, and the user is notified on the condition that the region of interest disappears from the image, or that the distance between the region of interest and the edge of the image is less than a predetermined threshold distance.

Supplementary Note 52

A cerebral aneurysm coil embolization assistance system, which is a system equipped with an image processing apparatus and an image capture device that captures and transmits to the image processing apparatus X-ray images of a patient in a state with a guiding catheter and a delivery wire for an embolic coil inserted into a blood vessel, wherein the image processing apparatus is equipped with an image acquisition unit that acquires X-ray images over time of a fixed area that includes at least the aneurysm in the patient's blood vessel, a catheter inserted into the blood vessel and a delivery wire for an embolization coil, a region of interest acquisition unit that acquires one or more areas that include at least a portion of the guiding catheter in the image as a region of interest, a marker detection unit that detects a marker provided on the delivery wire, which is a marker that approaches one or more regions of interest set in a portion of the catheter guiding the delivery wire, a tracking unit that tracks each of the regions of interest and the markers in the image, and a notification unit that notifies the user of the timing when the embolic coil may be detached from the delivery wire, triggered by the superimposition of the marker and the region of interest.

Supplementary Note 53

The system according to Supplementary Note 51 or 52, wherein the notification unit displays the distance between the region of interest and the edge portion of the image or the distance between the marker and the region of interest on a display device that displays the image, and wherein the notification unit can change the manner in which the distance is displayed on the display device according to the length of the distance, wherein the change in the display mode includes changing the font, size, or color of the characters displayed according to the length of the distance, changing the color of the entire screen or a portion of the screen of the display device according to the length of the distance, displaying a graphic on the entire screen or outside the frame of the display device or in a part of the screen, enlarging and displaying the region of interest according to the length of the distance, or changing the color or size of the mark attached to the region of interest according to the length of the distance.

Supplementary Note 54

The system according to any one of Supplementary Notes 51 to 53, wherein the notification unit can sound a notification tone or transmit vibration according to the length of the distance.

Supplementary Note 55

The system according to any one of Supplementary Notes 51 to 54, wherein the distance is determined by either a straight line distance or a distance along a blood vessel.

Supplementary Note 56

A cerebral aneurysm coil embolization assistance system, which is a system equipped with an image processing apparatus and an image capture device that captures and transmits to the image processing apparatus X-ray images of a patient in a state with a guiding catheter and a delivery wire for an embolic coil inserted into a blood vessel, wherein the image processing apparatus is equipped with a positional storage unit that stores the positional relationship between the tip of the catheter and a 2nd marker, a positional storage unit that stores the distance a between the neckline of the aneurysm and a 1st marker and the position of the 2nd marker at that time t1, a distance estimation unit that calculates the distance moved b from the position of the 2nd marker at time t2 and estimates the distance a-b from the aneurysm neckline to the tip of the catheter, and a notification unit that notifies the user of the estimated distance.

Supplementary Note 57

The system according to Supplementary Note 546, wherein the estimated distance is expressed by a probability distribution.

Supplementary Note 58

The system according to Supplementary Note 56 or 57, wherein the estimated position of the catheter tip is colored and displayed based on a probability distribution.

Supplementary Note 59

An endovascular surgical support system, comprising a storage unit that stores a product list of devices for examination or treatment in a blood vessel, a recommendation unit that recommends products for use based on image analysis results, facility information, or user preference information, and a display unit that displays the recommended products

1 . . . Image processing apparatus
10 . . . Storage unit
11 . . . Control unit
110 . . . Image acquisition unit
111 . . . Region of interest acquisition unit
112 . . . Tracking unit
113 . . . Notification unit
114 . . . Marker detection unit
115 . . . Distance measuring unit
2 . . . Display device
3 . . . X-ray image capture device
30 . . . X-ray irradiator
31 . . . X-ray detector
32 . . . Bed
D . . . Device
E . . . Coil for embolization
P . . . Test subject
S . . . Image processing system

The invention claimed is:

1. An image processing apparatus for assisting vascular catheterization, comprising:

a memory;

a processor that is connected to the memory, the processor configured to:

acquire a real-time image including at least a device for examination or treatment in a blood vessel as a photographic subject from an X-ray imaging apparatus connected to the processor, acquire one or more regions in the image that include at least a portion of the device as one or more regions of interest by using an object detection algorithm, track each of the regions of interest in the image by using a tracking algorithm, and cause a notification when at least one of the regions of interest satisfy one of conditions determined for each of the regions of interest, the conditions being conducive to ensuring medical safety, wherein the processor is configured to acquire real-time X-ray images of a fixed region over time including at least an area of interest for achieving a surgical objective of vascular catheterization and a device inserted into a blood vessel, wherein the conditions include that a distance between the region of interest and an edge of the image is less than a predetermined threshold distance, and/or that the region of interest exceeds a specific range specified on the image, wherein a boundary line of the specific range is represented by a straight line, a curve, a circle, a rectangle, or any other polygon, and wherein the specific range is superimposed and configured to be displayed on an X-ray image in a display device, the display device being connected to the processor.

2. The image processing apparatus according to claim 1, wherein the region of interest is set as a region including a tip portion of a catheter, the tip portion of a guide wire, a filter, a balloon, a liquid embolic material, a coil, a marker of a catheter, or a marker of a delivery wire of the coil.

3. The image processing apparatus according to claim 1, wherein the display device connected to the processor is further configured to:

i) display the distance between the region of interest and the edge portion of the image on the display device for displaying the image, and/or ii) change a display mode of the distance in the display device according toa length of the distance between the region of interest and the edge portion of the image.

4. The image processing apparatus according to claim 1, wherein a feature value associated with the region of interest is curvature, and wherein the processor is further configured to cause the notification to a user on the condition that the curvature of the device included in the region of interest exceeds a predetermined threshold curvature or that the curvature is changing but a tip portion of a catheter is not moving.

5. The image processing apparatus according to claim 1, wherein the processor is further configured to cause the notification to a user on the condition that a length of the device in the image or region of interest minus the length of a centerline of the blood vessel in the image or region of interest exceeds a predetermined threshold length.

6. The image processing apparatus according to claim 1, wherein the processor is further configured to cause the notification to a user by coloring the region of interest with a different color from the image, changing a font, size, or color of characters displayed, changing the color of an entire screen or part of the screen of the display device, displaying a graphic on the entire screen, outside a frame, or in some other location of the display device, enlarging the region of interest, or changing the color or size of a mark attached to the region of interest.

7. The image processing apparatus according to claim 1, wherein the processor is further configured to cause the notification to a user on the condition that at least one of:

i) the region of interest has moved;

ii) the region of interest disappears from the image;

iii) at least one of a movement distance, a movement speed, and an acceleration of the region of interest in the image exceeds a predetermined threshold value;

iv) the value obtained by dividing the distance between the region of interest and the edge of the image by the movement speed of the region of interest in the image is less than a predetermined threshold value; or v) a feature value associated with the region of interest indicating a shape of the device included in the region of interest satisfies a predetermined condition.

8. The image processing apparatus according to claim 1, wherein the memory connected to the processor is further configured to store images or videos obtained by the processor over time; and processor is further configured to extract video images from the memory for at least one of (1) a certain period of time before and after the notification is issued by the processor, or (2) at any time point or any period of time specified by a user, wherein the extracted video is displayed on a display device.

9. The image processing apparatus according to claim 1, wherein the display device displaying the image is further configured to display two images on two screens of the same size or two screens of different sizes, and wherein the display device is further configured to call attention to a user by at least one of making a frame portion of one of the two screens glow, changing a color, or highlighting the screen when the condition for notification is met.

10. The image processing apparatus according to claim 1, wherein the display device displaying the image is further configured to display a product list of devices for endovascular examination or treatment.

11. The image processing apparatus of claim 1, wherein the processor is further configured to, automatically or based on a user selection, create a surgical record that includes information of the device used, information of the images acquired, and a result of a processing of the image by the image processing apparatus.

12. The image processing apparatus of claim 1, wherein the processor is further configured to cause display on a display device a numerical value, color, bar or heat map according to a probability that at least one of the regions of interest satisfies a condition defined for each of the regions of interest, or the numerical value, the color, the bar or heat map based on any transformation applied to a distribution of the probability.

13. The image processing apparatus of claim 1, wherein the processor is further configured to color the region of interest with a color or heat map according to a probability that at least one of the regions of interest satisfies a condition defined for each of the regions of interest, or with a color or heat map based on an arbitrarily transformed value of a distribution of the probability, and cause display of it on the display device displaying the image, or alternatively, replaces the probability that satisfies the condition with a numerical value or color and displays it on the display device displaying the image.

14. The image processing apparatus according to claim 1, wherein the processor is further configured to acquire and store a position and/or shape of the device for examination or treatment in a blood vessel at any point in time, wherein the stored device position and/or shape are superimposed on images since acquisition.

15. The image processing apparatus according to claim 1, wherein the processor is further configured to recognize a lesion in the image selected from the group consisting of: aneurysm, stenosis, vasospasm, dissection, occlusion, recanalization, thrombosis, site of thrombus and location of both ends, vascular perforation, leakage of contrast medium out of a blood vessel, calcification of blood vessels, arteriosclerosis, shunt disease and its feeding and draining vessels, blood (contrast medium) backflow, cerebral arteriovenous malformations, dural arteriovenous fistulas, avascular region, characteristic anatomy of bones (internal auditory canal, ocular fundus, supraorbital margin, pyramidal body, foramen magnum occipitalis, cervical spine, clavicle, rib and spine numbers, femoral head, pelvis), feeding vessels of tumor and tumor staining, venous occlusion, venous sinus thrombosis, avascular area of capillary phase, vascular occlusion, coil shape and distribution within aneurysm, balloon position, inflation, and shape, coil deviation into a normal vessel, insufficient expansion of stent, degree of adherence to the vessel and torsion of stent, stent migration, position of stent at both ends, positional relationship between puncture site and blood vessel (no stenosis, none near bifurcation), vessel tortuosity, type of aortic arch (how far down from a top of the aortic arch that a right brachiocephalic artery is), extent of penetration of liquid embolic material, delay or stagnation of blood (contrast medium) flow, blood vessel variations (anterior communicating artery, anterior cerebral artery A1, posterior communicating artery, posterior cerebral artery P1, posterior inferior cerebellar artery, anterior inferior cerebellar artery, superior cerebellar artery, superficial temporal artery, presence and development of each venous sinus and each venous vein), moyamoya vessels of moyamoya disease (stenosis and occlusion of a tip of an internal carotid artery and development of collateral vessels beyond it), location of arterial bifurcations and segments (internal carotid artery conus, cavernous sinus, ophthalmic artery, middle cerebral artery M1 bifurcation), past surgery devices (clips, coils, plates, shunt tubes/valves, ventricular tubes and cistern tubes), position/openness of WEB devices, foreign bodies (dentures, plates), and collateral circulation.

16. The image processing apparatus according to claim 1, wherein the processor is further configured to compare the image in the image with a previously acquired and stored angiographic image and cause notification of a change.

17. The image processing apparatus according to claim 1, wherein the processor is further configured to change a manner in which the distance is displayed on the display device according to a length of the distance, wherein the change in a display mode includes changing a font, size, or color of characters displayed according to the length of the distance, changing the color of an entire screen or a portion of the screen of the display device according to the length of the distance, enlarging and displaying the region of interest according to the length of the distance, or changing the color or size of a mark attached to the region of interest according to the length of the distance.

18. The image processing apparatus according to claim 1, wherein the processor is further configured to cause a sound of the notification as tone, voice, or any kind of sound or transmit vibration according to a length of the distance.

* * * * *